US012357751B2

(12) United States Patent
    Coker et al.

(10) Patent No.: US 12,357,751 B2
(45) Date of Patent: Jul. 15, 2025

(54) LINEAR INSERTION DEVICE WITH ROTATIONAL DRIVE

(71) Applicant: CAPILLARY BIOMEDICAL, INC., Irvine, CA (US)

(72) Inventors: Justin Coker, Laguna Niguel, CA (US); Mark A. DeStefano, Collegeville, PA (US); Kenneth C. Hsu, Tustin, CA (US); Amber Stansberry, Irvine, CA (US); Paul Strasma, Irvine, CA (US); David Gillett, San Diego, CA (US); Mark Estes, Malibu, CA (US); Amrith Karunaratne, Irvine, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 1102 days.

(21) Appl. No.: 17/289,009

(22) PCT Filed: Nov. 8, 2019

(86) PCT No.: PCT/US2019/060602
§ 371 (c)(1),
(2) Date: Apr. 27, 2021

(87) PCT Pub. No.: WO2020/097552
PCT Pub. Date: May 14, 2020

(65) Prior Publication Data
US 2021/0402084 A1    Dec. 30, 2021

Related U.S. Application Data

(60) Provisional application No. 62/757,684, filed on Nov. 8, 2018.

(51) Int. Cl.
*A61M 5/142* (2006.01)
*A61M 5/158* (2006.01)
(Continued)

(52) U.S. Cl.
CPC ........ *A61M 5/158* (2013.01); *A61M 5/14248* (2013.01); *A61M 25/0113* (2013.01);
(Continued)

(58) Field of Classification Search
CPC ........... A61M 2005/14252; A61M 2025/0246; A61M 2039/0205; A61M 2005/1585;
(Continued)

(56) References Cited

U.S. PATENT DOCUMENTS 4,498,843 A    2/1985    Schneider et al.
4,703,756 A    11/1987   Gough et al.
(Continued)

FOREIGN PATENT DOCUMENTS

CA    2659005 C    4/2014
CA    2950966 C    7/2019
(Continued)

OTHER PUBLICATIONS

Oberg et al.; U.S. Appl. No. 17/446,271 entitled "Insulin infusion set," filed Aug. 27, 2021.
(Continued)

*Primary Examiner* — Deanna K Hall
(74) *Attorney, Agent, or Firm* — Merchant & Gould P.C.

(57) ABSTRACT

A system for delivering fluid to a user transcutaneously includes a torsion spring, a drive wheel, a linear slide having a stylet attached thereto, and a cannula. The torsion spring, when actuated, is configured to rotate the drive wheel to cause the linear slide to move axially to drive the stylet and cannula into a user-s skin.

27 Claims, 40 Drawing Sheets

(51) Int. Cl.
*A61M 25/01* (2006.01)
*A61M 25/06* (2006.01)
*A61M 25/02* (2006.01)

(52) U.S. Cl.
CPC .................. *A61M 25/0606* (2013.01); *A61M 2005/14252* (2013.01); *A61M 2005/1585* (2013.01); *A61M 2025/0246* (2013.01)

(58) Field of Classification Search
CPC ... A61M 39/04; A61M 5/14248; A61M 5/158
See application file for complete search history.

(56) References Cited

U.S. PATENT DOCUMENTS

| | | | |
|---|---|---|---|
| 4,755,173 A | 7/1988 | Konopka et al. |
| 4,777,953 A | 10/1988 | Ash et al. |
| 4,952,207 A | 8/1990 | Lemieux |
| 5,002,054 A | 3/1991 | Ash et al. |
| 5,176,662 A | 1/1993 | Bartholomew et al. |
| 5,425,723 A | 6/1995 | Wang |
| 5,545,152 A | 8/1996 | Funderburk et al. |
| 5,584,831 A | 12/1996 | McKay |
| 5,704,926 A | 1/1998 | Sutton |
| 5,848,996 A | 12/1998 | Eldor |
| 5,869,774 A | 2/1999 | Backlund et al. |
| 5,879,367 A | 3/1999 | Latterell et al. |
| 5,899,891 A | 5/1999 | Racz |
| 5,919,369 A | 7/1999 | Ash |
| 5,925,018 A | 7/1999 | Ungerstedt |
| 5,947,953 A | 9/1999 | Ash et al. |
| 5,995,860 A | 11/1999 | Sun et al. |
| 6,017,361 A | 1/2000 | Mikus et al. |
| 6,030,358 A | 2/2000 | Odland |
| 6,042,561 A | 3/2000 | Ash et al. |
| 6,042,576 A | 3/2000 | De Vries |
| 6,049,727 A | 4/2000 | Crothall |
| 6,056,718 A | 5/2000 | Funderburk et al. |
| 6,122,536 A | 9/2000 | Sun et al. |
| 6,179,816 B1 | 1/2001 | Mattola et al. |
| 6,261,272 B1 | 7/2001 | Gross et al. |
| 6,302,866 B1 | 10/2001 | Marggi |
| 6,304,766 B1 | 10/2001 | Colvin, Jr. |
| 6,471,689 B1 | 10/2002 | Joseph et al. |
| 6,488,663 B1 | 12/2002 | Steg |
| 6,537,241 B1 | 3/2003 | Odland |
| 6,572,542 B1 | 6/2003 | Houben et al. |
| 6,572,586 B1 | 6/2003 | Wojcik |
| 6,585,695 B1 | 7/2003 | Adair et al. |
| 6,618,603 B2 | 9/2003 | Varalli et al. |
| 6,702,857 B2 | 3/2004 | Brauker et al. |
| 6,736,797 B1 | 5/2004 | Larsen et al. |
| 6,749,589 B1 | 6/2004 | Douglas et al. |
| 6,770,030 B1 | 8/2004 | Schaupp et al. |
| 6,800,451 B2 | 10/2004 | Daniloff et al. |
| 6,805,683 B1 | 10/2004 | Johansson |
| 6,830,562 B2 | 12/2004 | Mogensen |
| 6,855,136 B2 | 2/2005 | Dorros et al. |
| 6,862,534 B2 | 3/2005 | Sterling et al. |
| 6,929,618 B1 | 8/2005 | Johansson |
| 6,940,590 B2 | 9/2005 | Colvin, Jr. et al. |
| 6,989,891 B2 | 1/2006 | Braig et al. |
| 7,009,180 B2 | 3/2006 | Sterling et al. |
| 7,022,071 B2 | 4/2006 | Schaupp et al. |
| 7,052,483 B2 | 5/2006 | Wojcik |
| 7,070,580 B2 | 7/2006 | Nielsen |
| 7,128,727 B2 | 10/2006 | Flaherty et al. |
| 7,147,623 B2 | 12/2006 | Mathiasen |
| 7,157,723 B2 | 1/2007 | Colvin et al. |
| 7,211,068 B2 | 5/2007 | Douglas |
| 7,235,350 B2 | 6/2007 | Schulman et al. |
| 7,248,912 B2 | 7/2007 | Gough et al. |
| 7,255,687 B2 | 8/2007 | Huang et al. |
| 7,309,325 B2 | 12/2007 | Mulier et al. |
| 7,336,984 B2 | 2/2008 | Gough et al. |
| 7,364,592 B2 | 4/2008 | Carr-Brendel et al. |
| 7,588,558 B2 | 9/2009 | Sage, Jr. et al. |
| 7,593,108 B2 | 9/2009 | Sterling et al. |
| 7,613,491 B2 | 11/2009 | Boock et al. |
| 7,621,395 B2 | 11/2009 | Mogensen et al. |
| 7,637,918 B2 | 12/2009 | Dant |
| 7,651,845 B2 | 1/2010 | Doyle et al. |
| 7,666,172 B2 | 2/2010 | Atil |
| 7,686,787 B2 | 3/2010 | Moberg et al. |
| 7,699,808 B2 | 4/2010 | Marrs et al. |
| 7,722,537 B2 | 5/2010 | Sterling et al. |
| 7,744,570 B2 | 6/2010 | Fangrow, Jr. |
| 7,800,078 B2 | 9/2010 | Colvin, Jr. et al. |
| 7,822,450 B2 | 10/2010 | Colvin, Jr. et al. |
| 7,867,199 B2 | 1/2011 | Mogensen et al. |
| 7,867,200 B2 | 1/2011 | Mogensen et al. |
| 7,871,456 B2 | 1/2011 | Gough et al. |
| 7,875,008 B2 | 1/2011 | Chong et al. |
| 7,894,870 B1 | 2/2011 | Lucisano et al. |
| 7,905,877 B1 | 3/2011 | Jimenez et al. |
| 7,931,621 B2 | 4/2011 | Cross et al. |
| 7,935,092 B1 | 5/2011 | Odland et al. |
| 7,939,332 B2 | 5/2011 | Colvin, Jr. |
| 7,951,357 B2 | 5/2011 | Gross et al. |
| 7,985,199 B2 | 7/2011 | Komerup et al. |
| 8,012,126 B2 | 9/2011 | Tipsmark et al. |
| 8,043,229 B2 | 10/2011 | Mulvihill et al. |
| 8,062,250 B2 | 11/2011 | Mogensen et al. |
| 8,073,548 B2 | 12/2011 | Colvin, Jr. et al. |
| 8,114,064 B2 | 2/2012 | Alferness et al. |
| 8,143,068 B2 | 3/2012 | Colvin, Jr. et al. |
| 8,157,773 B2 | 4/2012 | Tashjian |
| 8,172,805 B2 | 5/2012 | Mogensen et al. |
| 8,204,565 B2 | 6/2012 | Arnold et al. |
| 8,206,343 B2 | 6/2012 | Racz |
| 8,229,546 B2 | 7/2012 | Falkén et al. |
| 8,273,061 B2 | 9/2012 | McConnell et al. |
| 8,273,228 B2 | 9/2012 | Dall'Oglio et al. |
| 8,303,533 B2 | 11/2012 | Regittnig et al. |
| 8,318,193 B2 | 11/2012 | Ratner et al. |
| 8,333,734 B2 | 12/2012 | Zohmann |
| 8,403,911 B2 | 3/2013 | Adams et al. |
| 8,415,184 B2 | 4/2013 | Colvin et al. |
| 8,502,167 B2 | 8/2013 | Colvin, Jr. et al. |
| 8,535,537 B2 | 9/2013 | Feichtner et al. |
| 8,562,567 B2 | 10/2013 | Gundberg |
| 8,604,810 B2 | 12/2013 | Sheppard |
| 8,608,729 B2 | 12/2013 | Christenson |
| 8,608,922 B2 | 12/2013 | Papadimitrakopoulos et al. |
| 8,647,393 B2 | 2/2014 | Marshall et al. |
| 8,708,994 B2 | 4/2014 | Pettis et al. |
| 8,827,979 B2 | 9/2014 | Pesach et al. |
| 8,945,057 B2 | 2/2015 | Gymn et al. |
| 8,971,981 B2 | 3/2015 | Yodfat et al. |
| 8,998,851 B2 | 4/2015 | Constantineau et al. |
| 9,084,848 B2 | 7/2015 | Schiltges et al. |
| 9,114,208 B2 | 8/2015 | Smith et al. |
| 9,131,960 B2 | 9/2015 | Racz |
| 9,180,244 B2 | 11/2015 | Anderson et al. |
| 9,192,717 B2 | 11/2015 | Cote et al. |
| 9,227,013 B2 | 1/2016 | Lacy |
| 9,375,529 B2 | 6/2016 | Searle et al. |
| 9,399,094 B2 | 7/2016 | Krag et al. |
| 9,463,889 B2 | 10/2016 | Schmitz et al. |
| 9,480,792 B2 | 11/2016 | Constantineau et al. |
| 9,522,229 B2 | 12/2016 | Sonderegger et al. |
| 9,579,452 B2 | 2/2017 | Adair et al. |
| 9,713,674 B2 | 7/2017 | Carter et al. |
| 9,782,536 B2 | 10/2017 | Skutnik et al. |
| 9,782,538 B2 | 10/2017 | Cole et al. |
| 9,821,113 B2 | 11/2017 | Cole et al. |
| 9,968,742 B2 | 5/2018 | Antwerp et al. |
| 10,076,605 B2 | 9/2018 | Marbet et al. |
| 10,080,839 B2 | 9/2018 | Cole et al. |
| 10,173,007 B2 | 1/2019 | Hayter et al. |
| 10,265,483 B2 | 4/2019 | Cole et al. |
| 10,413,658 B2 | 9/2019 | Gillett et al. |
| 10,420,489 B2 | 9/2019 | Kovatchev et al. |
| 10,434,285 B2 | 10/2019 | Schoonmaker et al. |

(56) References Cited

U.S. PATENT DOCUMENTS

| | | |
|---|---|---|
| 10,449,296 B2 | 10/2019 | Kapas et al. |
| 10,463,787 B2 | 11/2019 | Shor et al. |
| 10,675,403 B2 | 6/2020 | Montalvo et al. |
| 10,722,653 B2 | 7/2020 | Kapas et al. |
| 10,828,418 B2 | 11/2020 | Constantineau et al. |
| 10,943,687 B2 | 3/2021 | Blomquist |
| 11,160,922 B2 | 11/2021 | Just |
| 2002/0016614 A1* | 2/2002 | Klein ............... A61B 17/0469 606/224 |
| 2002/0123740 A1 | 9/2002 | Flaherty et al. |
| 2004/0075198 A1 | 4/2004 | Schweikert et al. |
| 2004/0143216 A1 | 7/2004 | Douglas et al. |
| 2004/0158207 A1 | 8/2004 | Hunn et al. |
| 2004/0236290 A1 | 11/2004 | Zimmermann |
| 2005/0137525 A1 | 6/2005 | Wang et al. |
| 2005/0192558 A1 | 9/2005 | Bernard et al. |
| 2005/0273076 A1 | 12/2005 | Beasley et al. |
| 2006/0100583 A1 | 5/2006 | Terzoli |
| 2006/0122536 A1 | 6/2006 | Haar et al. |
| 2006/0135941 A1 | 6/2006 | Porto et al. |
| 2006/0135981 A1 | 6/2006 | Lenker et al. |
| 2006/0211933 A1 | 9/2006 | Zimmermann et al. |
| 2007/0060834 A1 | 3/2007 | Odland et al. |
| 2007/0062251 A1 | 3/2007 | Anex |
| 2007/0282269 A1 | 12/2007 | Carter et al. |
| 2008/0091173 A1 | 4/2008 | Belley et al. |
| 2008/0108950 A1 | 5/2008 | Rioux et al. |
| 2008/0243085 A1 | 10/2008 | DeStefano |
| 2008/0269687 A1 | 10/2008 | Chong et al. |
| 2008/0287877 A1 | 11/2008 | Gresham et al. |
| 2008/0319414 A1 | 12/2008 | Yodfat et al. |
| 2009/0048563 A1 | 2/2009 | Ethelfeld et al. |
| 2009/0069750 A1 | 3/2009 | Schraga |
| 2009/0156926 A1 | 6/2009 | Messerly et al. |
| 2010/0063445 A1 | 3/2010 | Sternberg et al. |
| 2010/0160749 A1 | 6/2010 | Gross et al. |
| 2010/0286714 A1 | 11/2010 | Gymn et al. |
| 2010/0298830 A1 | 11/2010 | Browne et al. |
| 2010/0303772 A1 | 12/2010 | McMillan et al. |
| 2011/0099789 A1 | 5/2011 | Ewing et al. |
| 2012/0059320 A1 | 3/2012 | Maule et al. |
| 2012/0078226 A1 | 3/2012 | Dwanisa et al. |
| 2012/0265034 A1 | 10/2012 | Wisniewski et al. |
| 2013/0126349 A1 | 5/2013 | Zhang |
| 2013/0245555 A1 | 9/2013 | Dirac et al. |
| 2013/0338630 A1 | 12/2013 | Agrawal et al. |
| 2014/0025039 A1 | 1/2014 | Rajendran et al. |
| 2014/0031793 A1 | 1/2014 | Constantineau et al. |
| 2014/0058353 A1 | 2/2014 | Politis et al. |
| 2014/0088555 A1 | 3/2014 | Li et al. |
| 2015/0011970 A1 | 1/2015 | Kamen et al. |
| 2015/0051583 A1 | 2/2015 | Horvath et al. |
| 2015/0057611 A1 | 2/2015 | Bureau |
| 2015/0112302 A1 | 4/2015 | Chattaraj et al. |
| 2015/0165161 A1 | 6/2015 | Uber, III et al. |
| 2015/0182693 A1 | 7/2015 | Rosinko |
| 2015/0265767 A1 | 9/2015 | Varquez et al. |
| 2015/0283321 A1 | 10/2015 | Dang et al. |
| 2015/0290390 A1 | 10/2015 | Ring et al. |
| 2016/0106919 A1 | 4/2016 | Hayter et al. |
| 2016/0279325 A1 | 9/2016 | Searle et al. |
| 2016/0290390 A1 | 10/2016 | Ambroise et al. |
| 2017/0021096 A1 | 1/2017 | Cole et al. |
| 2017/0076068 A1 | 3/2017 | Dobbles et al. |
| 2017/0189614 A1 | 7/2017 | Mazlish et al. |
| 2018/0104411 A1 | 4/2018 | Chovanda et al. |
| 2018/0200412 A1 | 7/2018 | Dang et al. |
| 2018/0207356 A1 | 7/2018 | Joseph et al. |
| 2018/0220942 A1 | 8/2018 | El-Khatib et al. |
| 2018/0280608 A1* | 10/2018 | Gillett ............... A61M 5/158 |
| 2018/0369479 A1 | 12/2018 | Hayler et al. |
| 2019/0053742 A1 | 2/2019 | Steil et al. |
| 2019/0099555 A1 | 4/2019 | Patek et al. |
| 2019/0175840 A1 | 6/2019 | Schabbach et al. |
| 2019/0224409 A1 | 7/2019 | Sonderegger |
| 2019/0282753 A1 | 9/2019 | Gillett et al. |
| 2019/0388015 A1 | 12/2019 | Blomquist et al. |
| 2020/0147300 A1 | 5/2020 | Novak et al. |
| 2020/0155755 A1 | 5/2020 | Chaves et al. |
| 2020/0222625 A1 | 7/2020 | Cabiri et al. |
| 2020/0246541 A1 | 8/2020 | Neftel et al. |
| 2020/0345929 A1 | 11/2020 | Ben-David et al. |
| 2021/0016004 A1 | 1/2021 | El-Khatib et al. |
| 2021/0106803 A1 | 4/2021 | Kaiser-Pendergrast |
| 2021/0369957 A1 | 12/2021 | Wieser et al. |

FOREIGN PATENT DOCUMENTS

| | | |
|---|---|---|
| CN | 100366305 C | 2/2008 |
| CN | 101027095 B | 9/2010 |
| EP | 1608420 B1 | 11/2006 |
| EP | 2004241 B1 | 12/2008 |
| EP | 1951340 B1 | 8/2009 |
| EP | 2193814 A1 | 6/2010 |
| EP | 2457606 A1 | 5/2012 |
| EP | 2099384 B1 | 9/2018 |
| EP | 2560727 B1 | 2/2019 |
| EP | 3459574 A1 | 3/2019 |
| EP | 2254622 B1 | 5/2019 |
| EP | 2259815 B1 | 6/2019 |
| EP | 2350895 B1 | 6/2019 |
| EP | 3656417 A1 | 5/2020 |
| EP | 3698828 A1 | 8/2020 |
| EP | 3134150 B1 | 2/2021 |
| EP | 3576823 B1 | 3/2021 |
| WO | WO96/032981 A1 | 10/1996 |
| WO | WO01/034237 A1 | 5/2001 |
| WO | WO2007/140632 A1 | 12/2007 |
| WO | WO2010/084113 A1 | 7/2010 |
| WO | WO2012/073097 A2 | 6/2012 |
| WO | WO2012/118762 A1 | 9/2012 |
| WO | 2017127215 A1 | 7/2017 |
| WO | WO2017/125817 A1 | 7/2017 |
| WO | 2018070978 A1 | 4/2018 |
| WO | 2018165499 A1 | 8/2018 |
| WO | WO2018/184012 A1 | 10/2018 |

OTHER PUBLICATIONS

Bryant, J., Fluid dynamics—Equation of continuity and Bernoulli's principle; retrieved from the internet at http://www.physics.usyd.edu.au/~jbryant/Fluids/Fluidslect4.pdf on Apr. 2, 2015; 37 pages.

Calthorpe, N., The history of spinal needles: getting to the point; Anaesthesia; 59(12); pp. 1231-1241; Dec. 2004.

Campolo et al., Protocols to compare infusion distribution of wound catheters; Med. Eng. Phys.; 34(3); pp. 326-332; Apr. 2012.

Centers for Disease Control and Prevention (CDCP); National Diabetes Statistics Report, 2014—Estimates of Diabetes and Its Burden in the United States; U.S. Dept. of Health and Human Services, Atlanta, GA; 8 pgs.; (year of pub sufficiently earlier than effective US filing date and any foreign priority date) 2014.

Cho et al., On-line near-infrared spectrometer to monitor urea removal in real time during hemodialysis; Appl. Spectrosc.; 62(8); pp. 866-872; Aug. 2008.

Dziubla et al., Evaluation of porous networks of poly(2-hydroxyethyl methacrylate) as interfacial drug delivery devices; Biomaterials; 22(21); pp. 2893-2899; Nov. 2001.

Edsberg et al., Insulin bolus given by sprinkler needle: effect on absorption and glycaemic response to a meal; Br. Med. J. Clin. Res. Ed.; 294(6584); pp. 1373-1376; May 30, 1987.

Jockel et al., Insulin depot formation in subcutaneous tissue; J. Diabetes Sci. Technol.; 7(1); pp. 227-237; Jan. 2013.

Miller et al., Current state of type 1 diabetes treatment in the U.S.: updated data from the T1D Exchange clinic registry; Diabetes Care; 38(6); pp. 971-978; Jun. 2015.

Neithercott, T., Infusion Sets 2014—How to choose the kind of insulin delivery that's right for you; Diabetes Forecast ® ; (downloaded from the internet at http://www.diabetesforecast.org/2014/Jan/infusion-sets-2014.html on Dec. 6, 2018); Dec. 2013; 2 pgs.

(56) References Cited

OTHER PUBLICATIONS

Patel et al., Randomized trial of infusion set function: steel versus teflon; Diabetes Technol. and Ther.; 16(1); pp. 15-19; Jan. 2014.

Pfutzner et al., Improved Insulin Absorption by Means of Standardized Injection Site Modulation Results in a Safer and More Efficient Prandial Insulin Treatment; A Review of the Existing Clinical Data; J. Diabetes Sci. Technol.; 9(1); pp. 116-122; Jan. 2015.

Walsh et al., Insulin Pump and CGM Usage in the United States and Germany: Results of a Real-World Survey with 985 Subjects; J. Diabetes Sci. Technol.; 9(5); pp. 1103-1110; Sep. 2015.

Wootten et al., Broadband 2.4 μm superluminescent GaIn-AsSb/AlGaAsSb quantum well diodes for optical sensing of biomolecules; Semicond. Sci. Technol. (Internet); 29(11); Nov. 2014 doi: 10.1088/0268-1242/29/11/115,014; Avail. from http://www.ncbi.nlm.nih.gov/pmc/articles/PMC4283575/.

European Office Action, Application No. 19881515.1, Dated Oct. 4, 2024.

\* cited by examiner

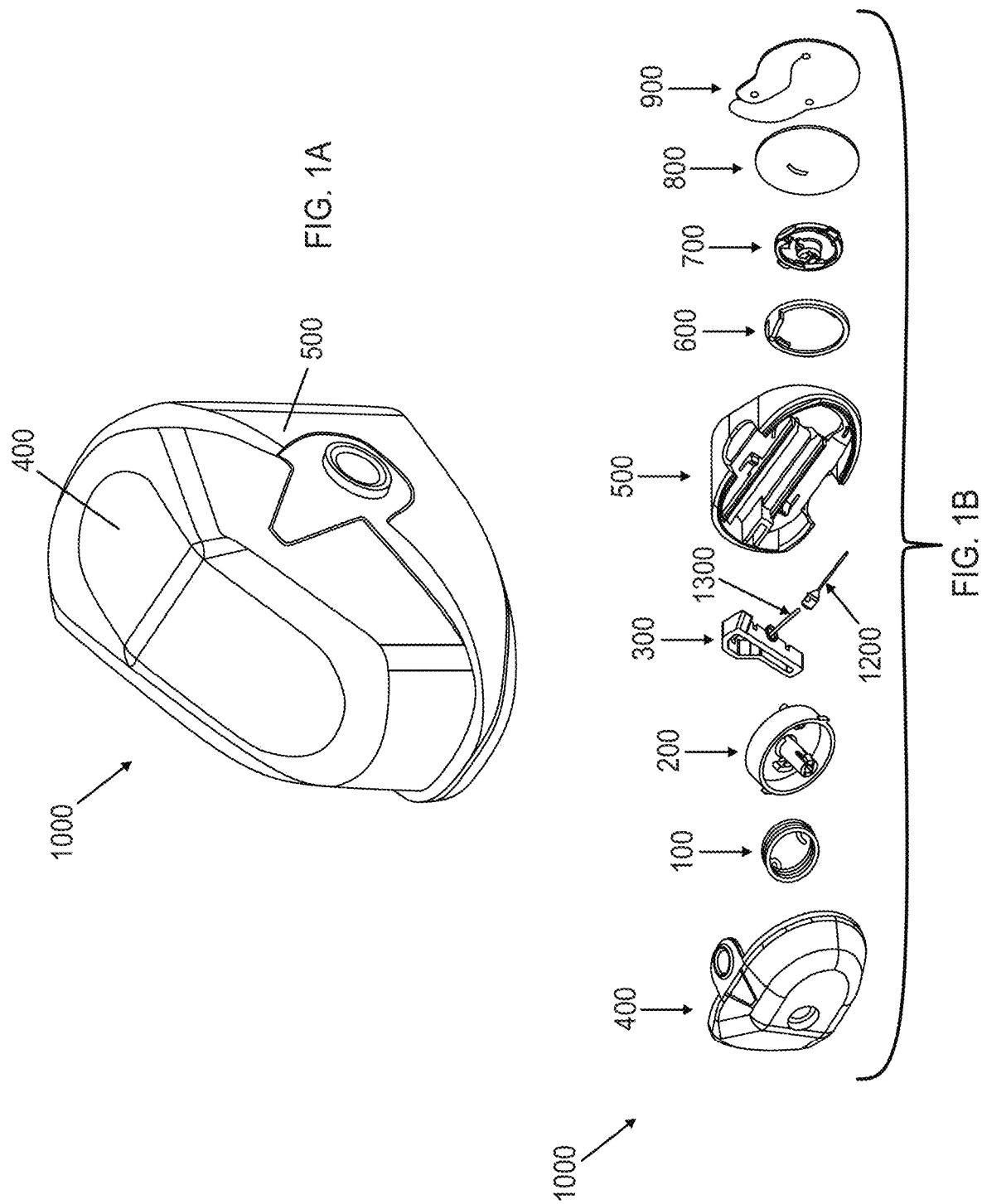

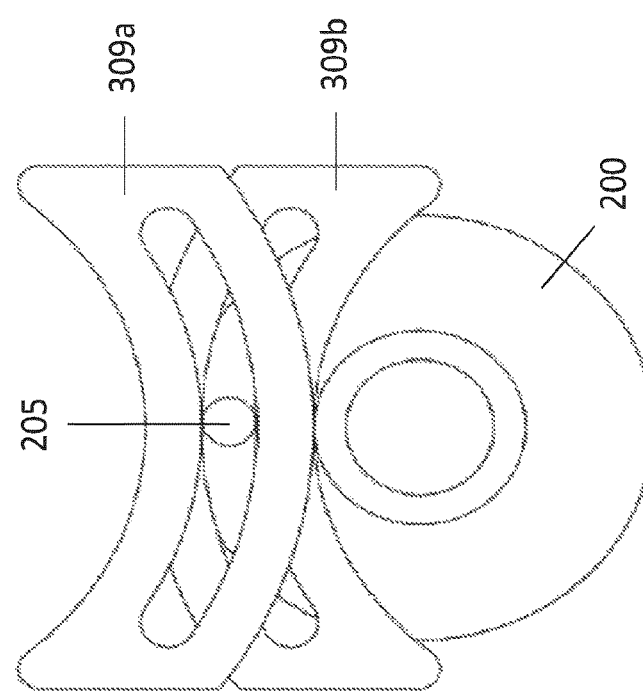

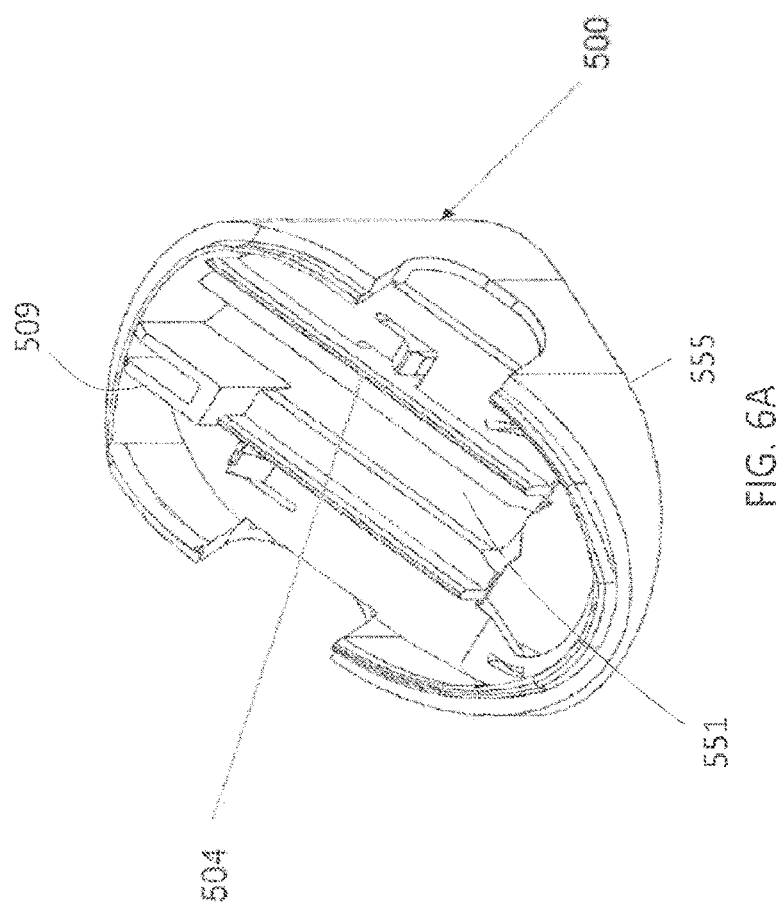

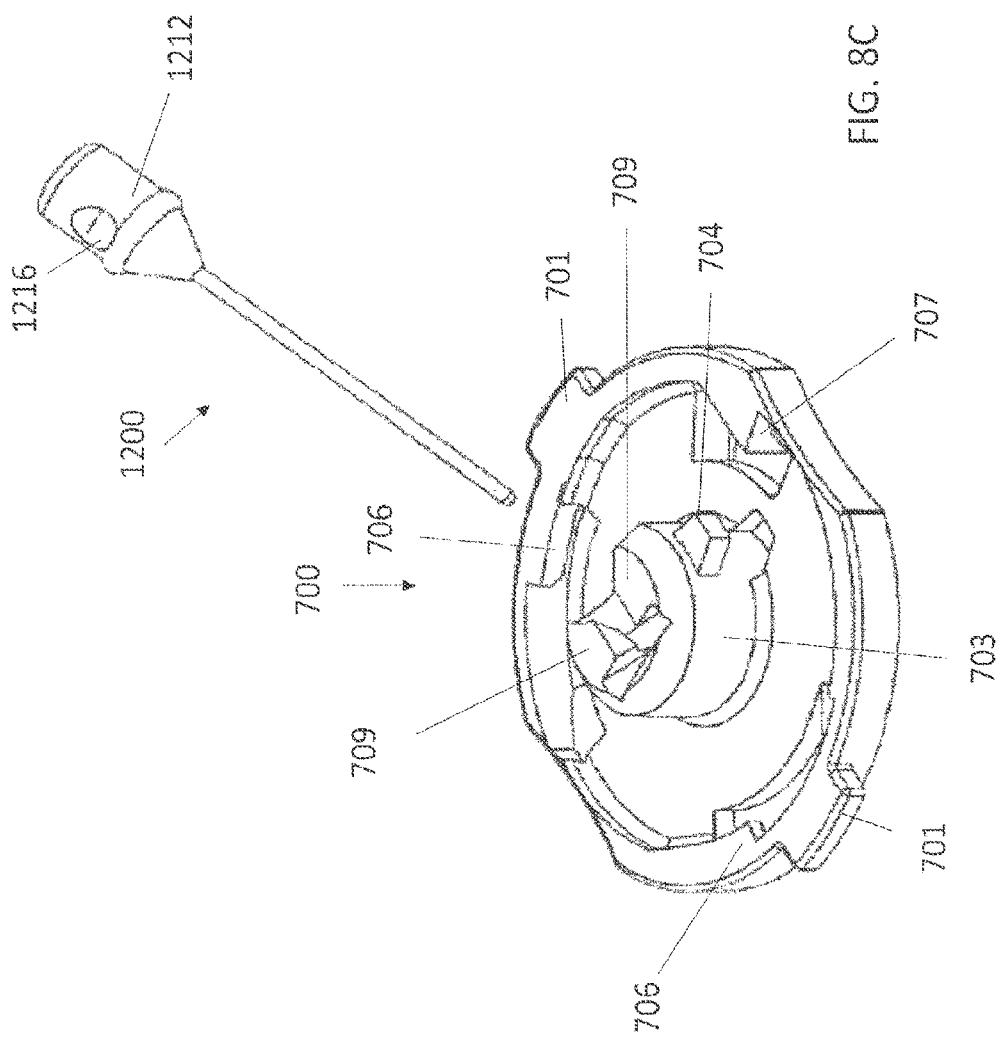

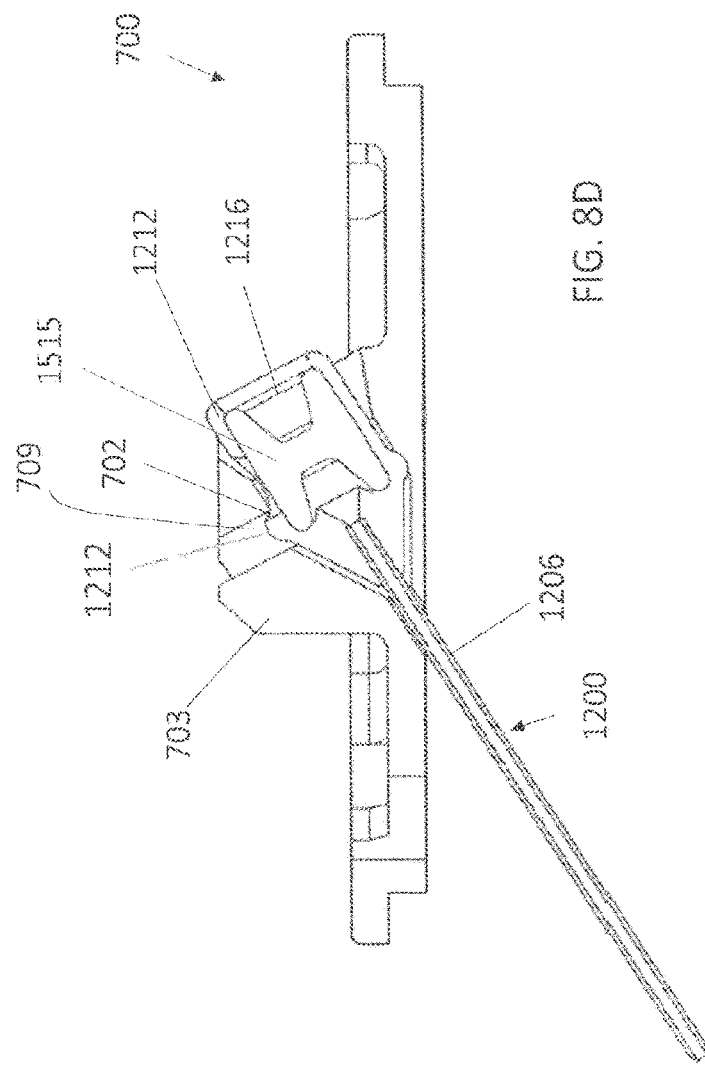

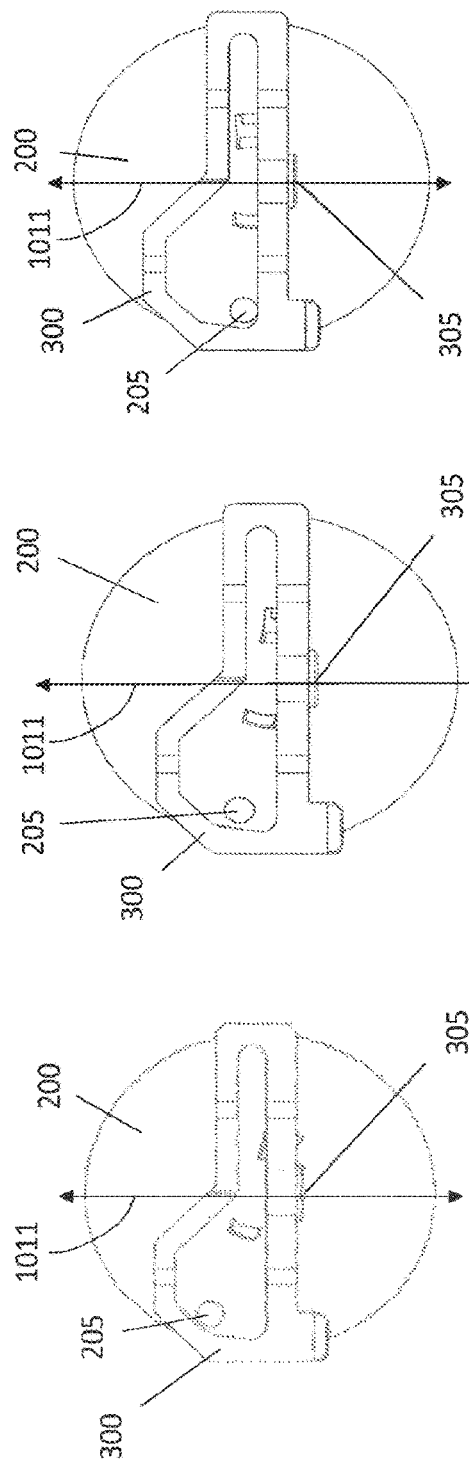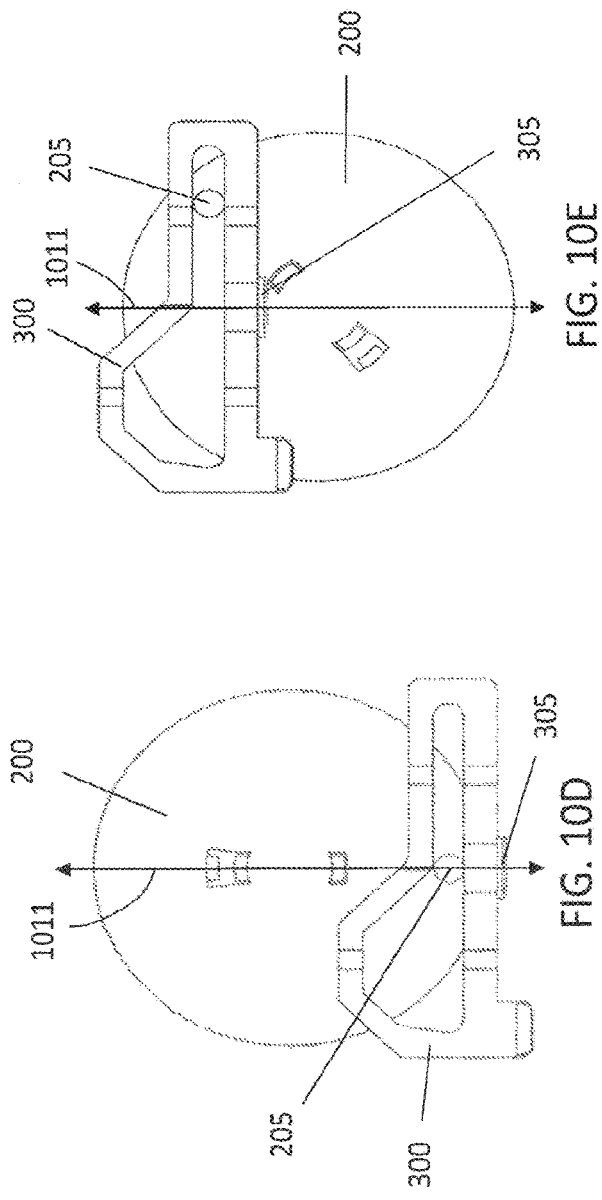

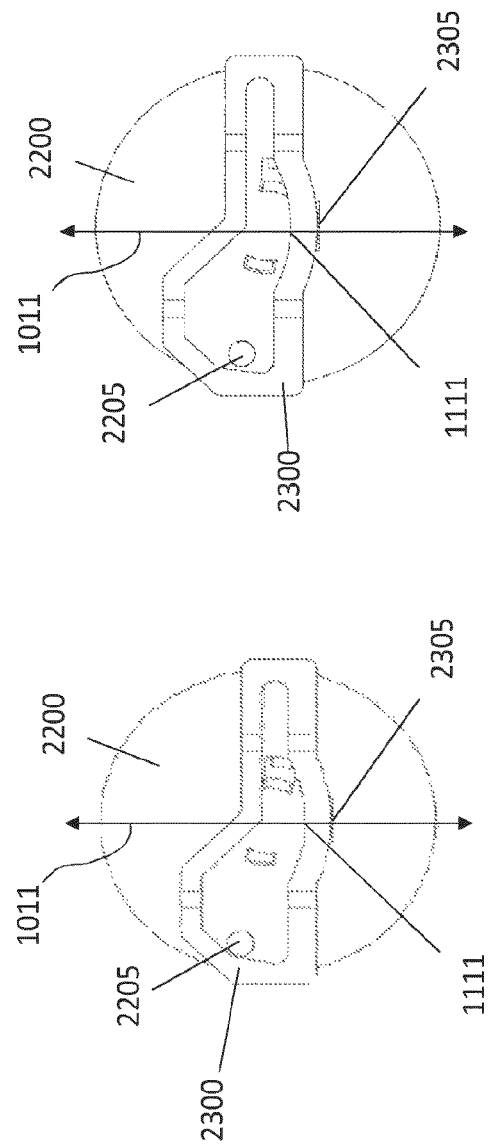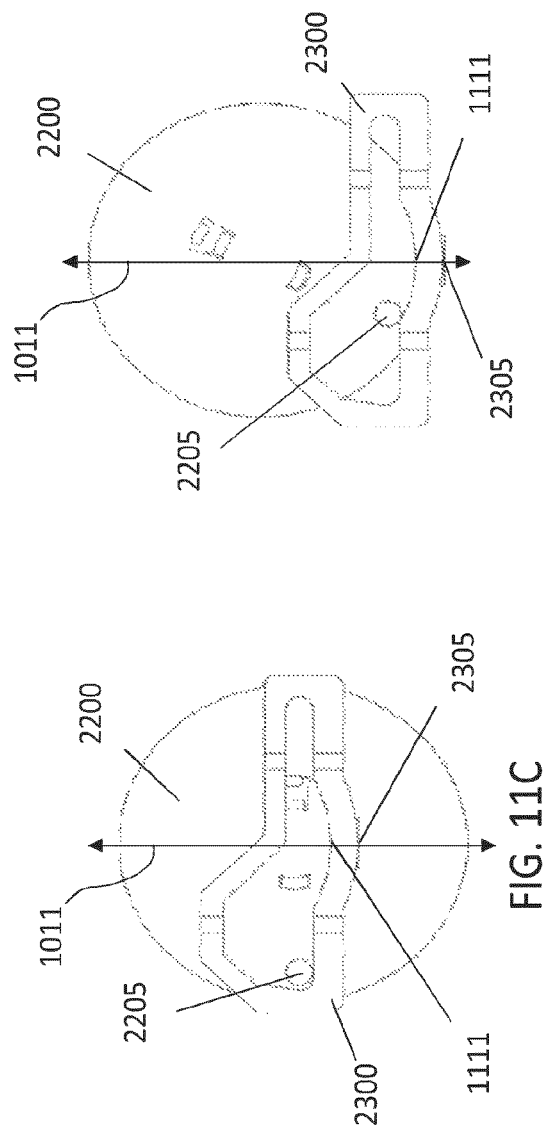
FIG. 11A
FIG. 11B
FIG. 11C
FIG. 11D

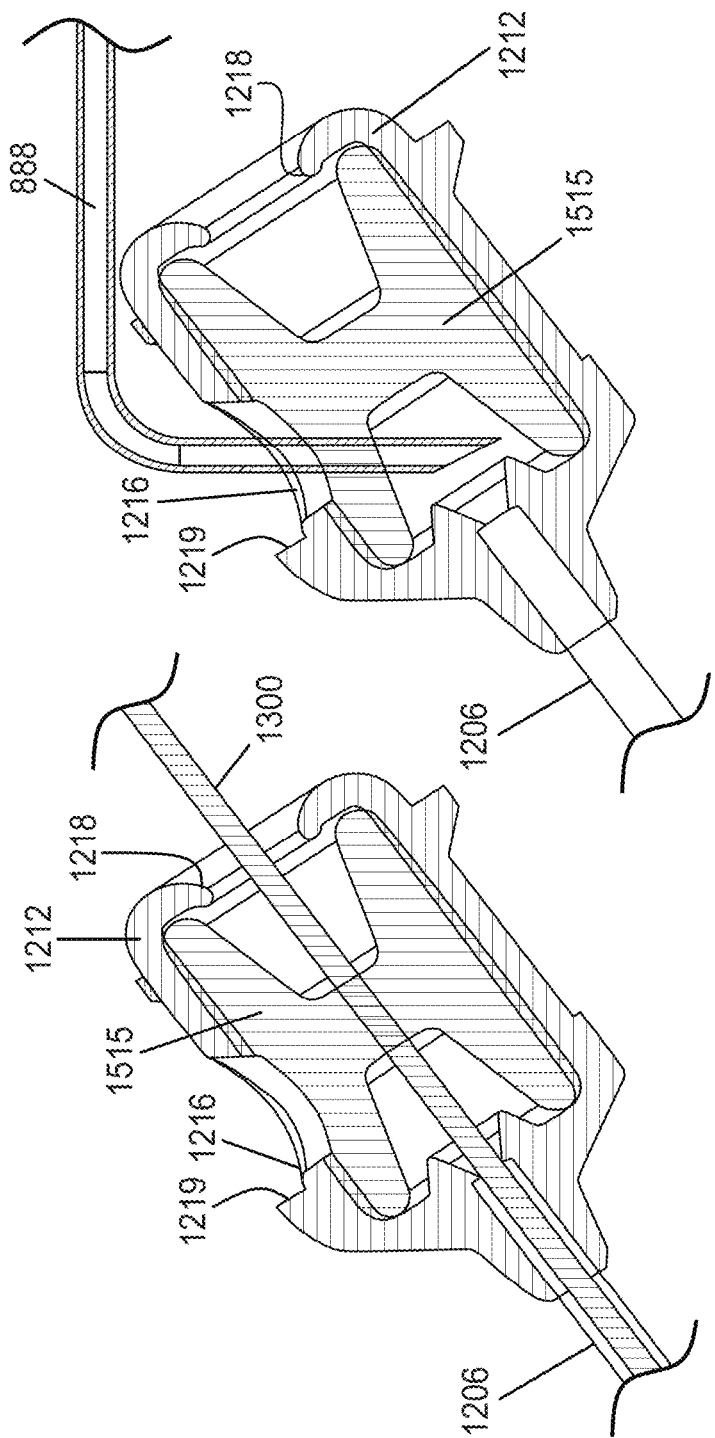

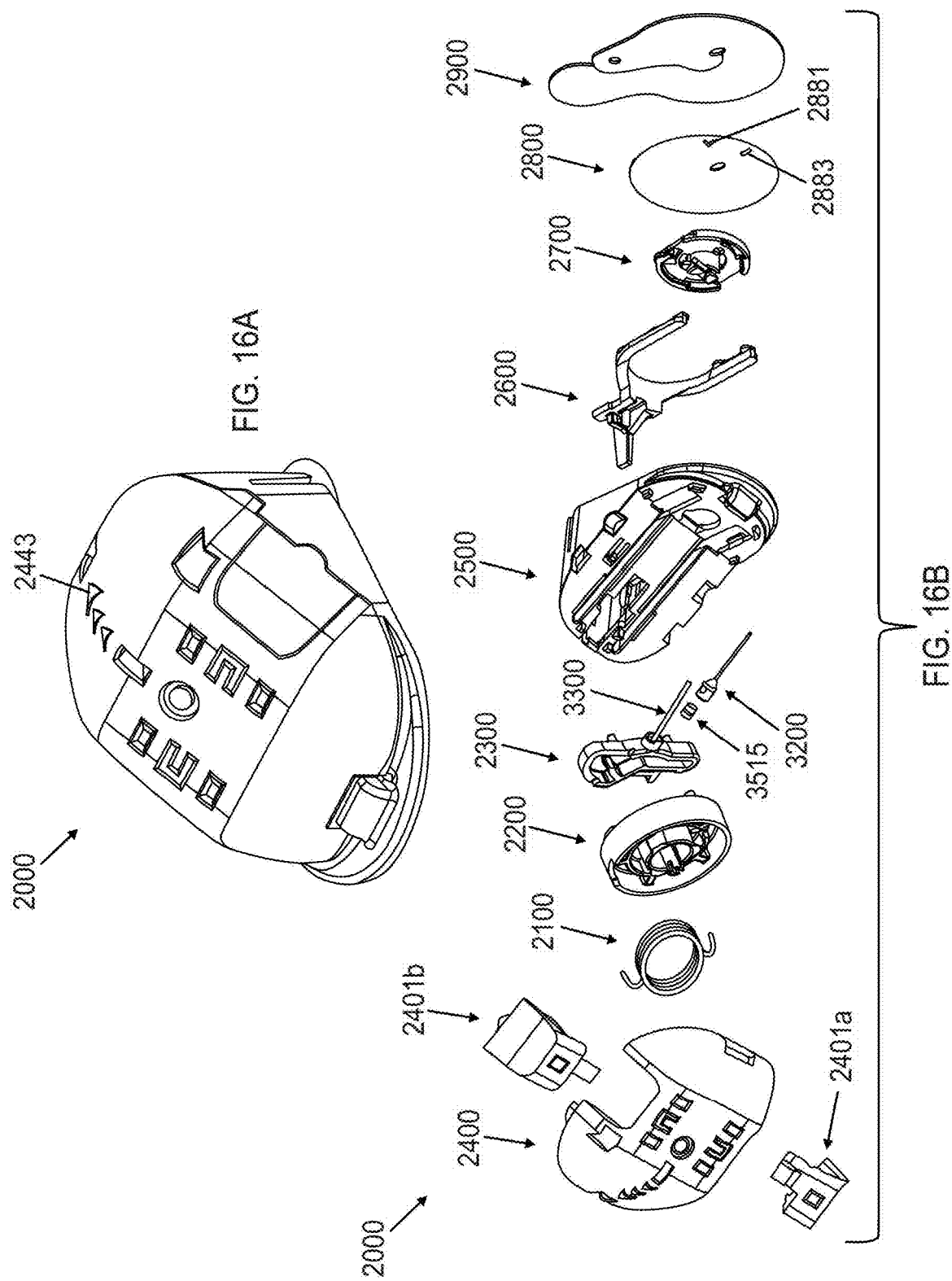

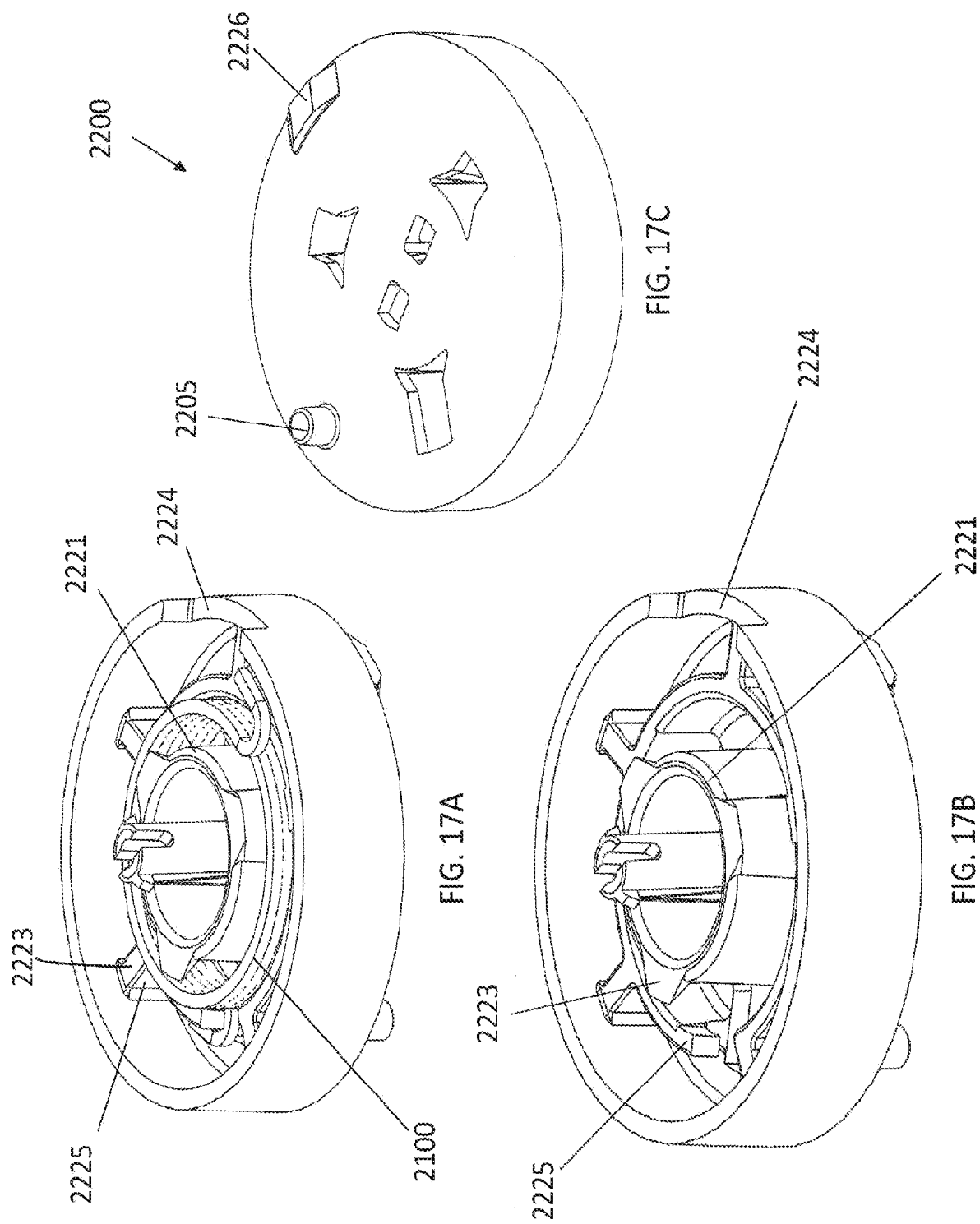

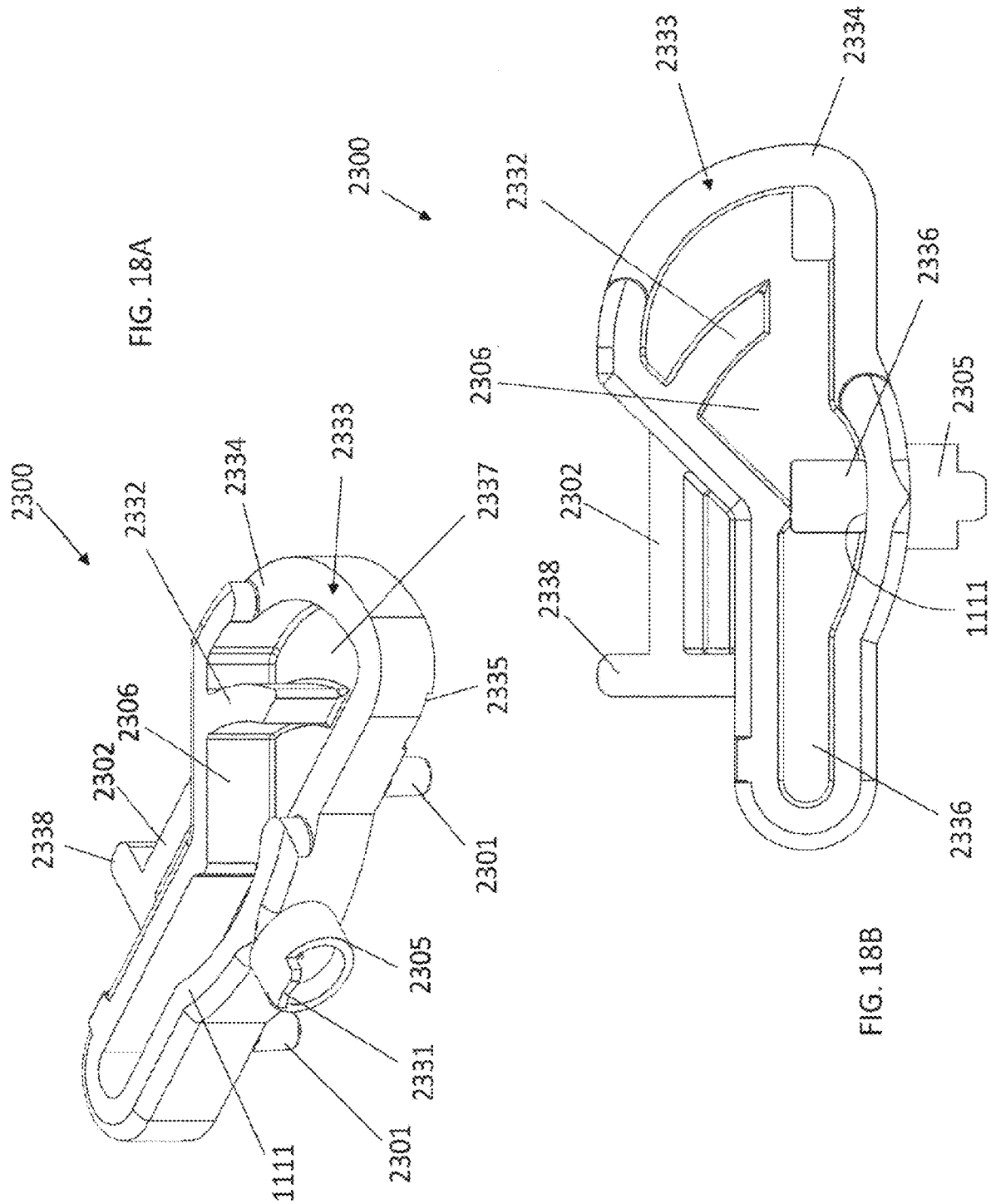

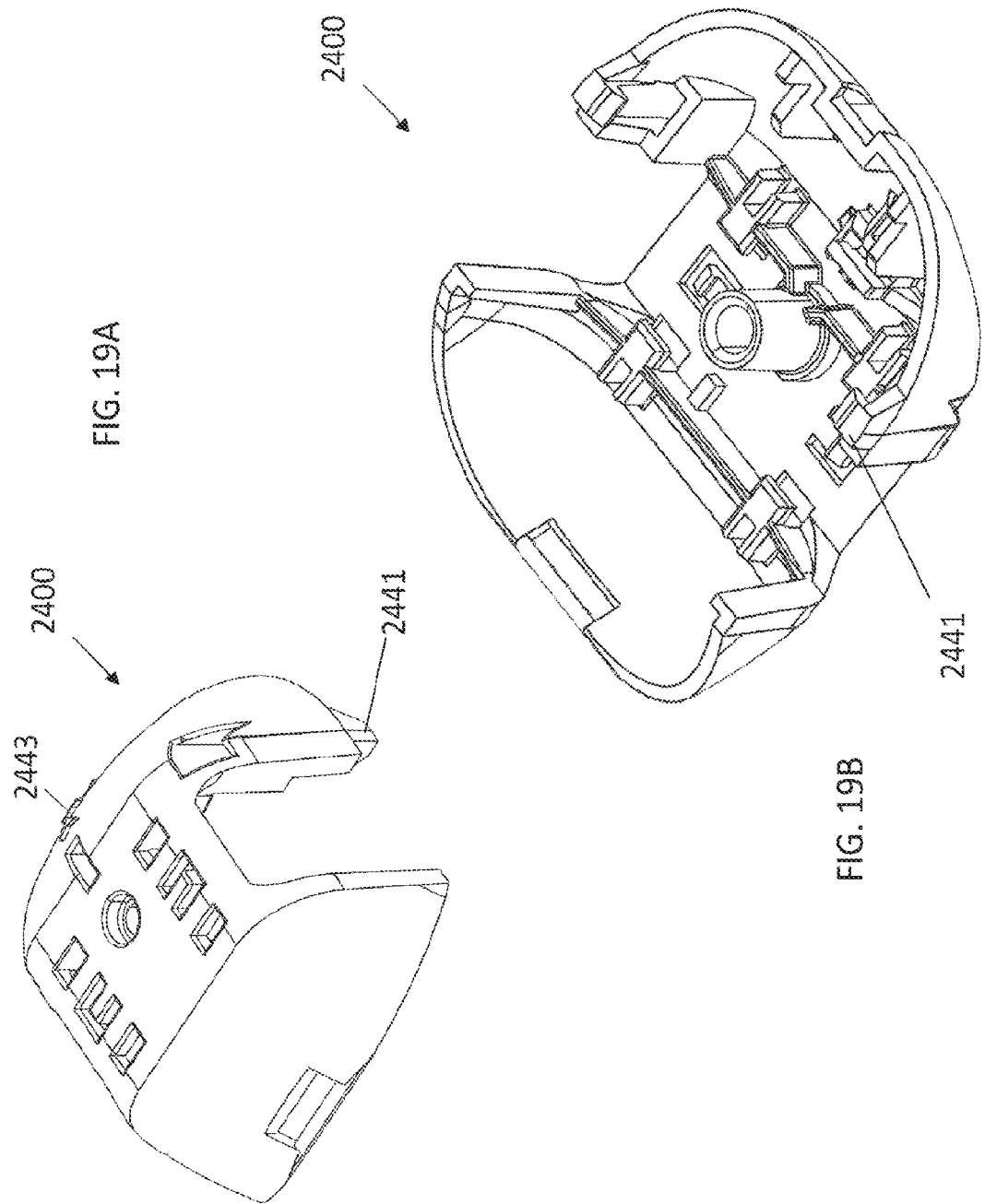

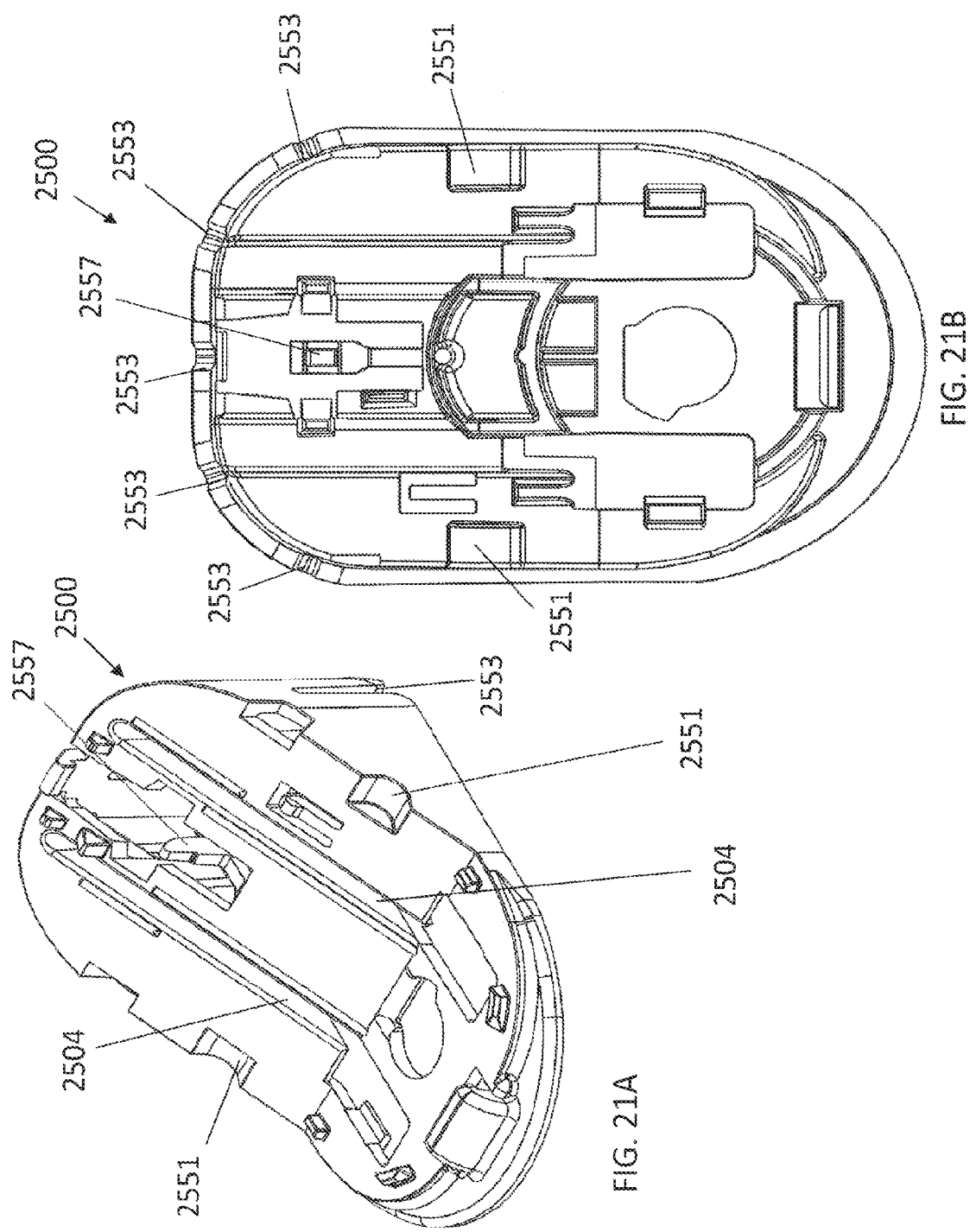

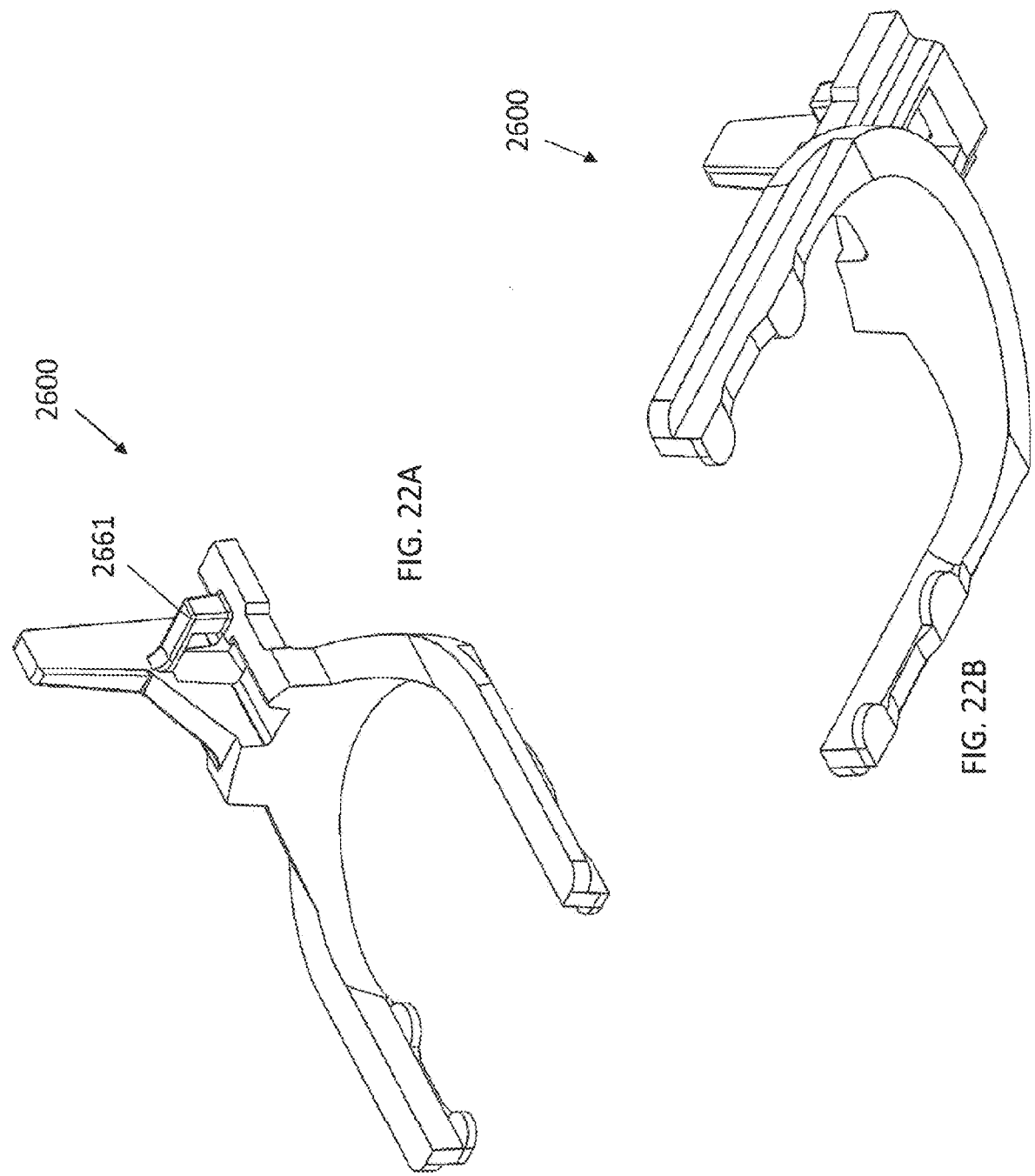

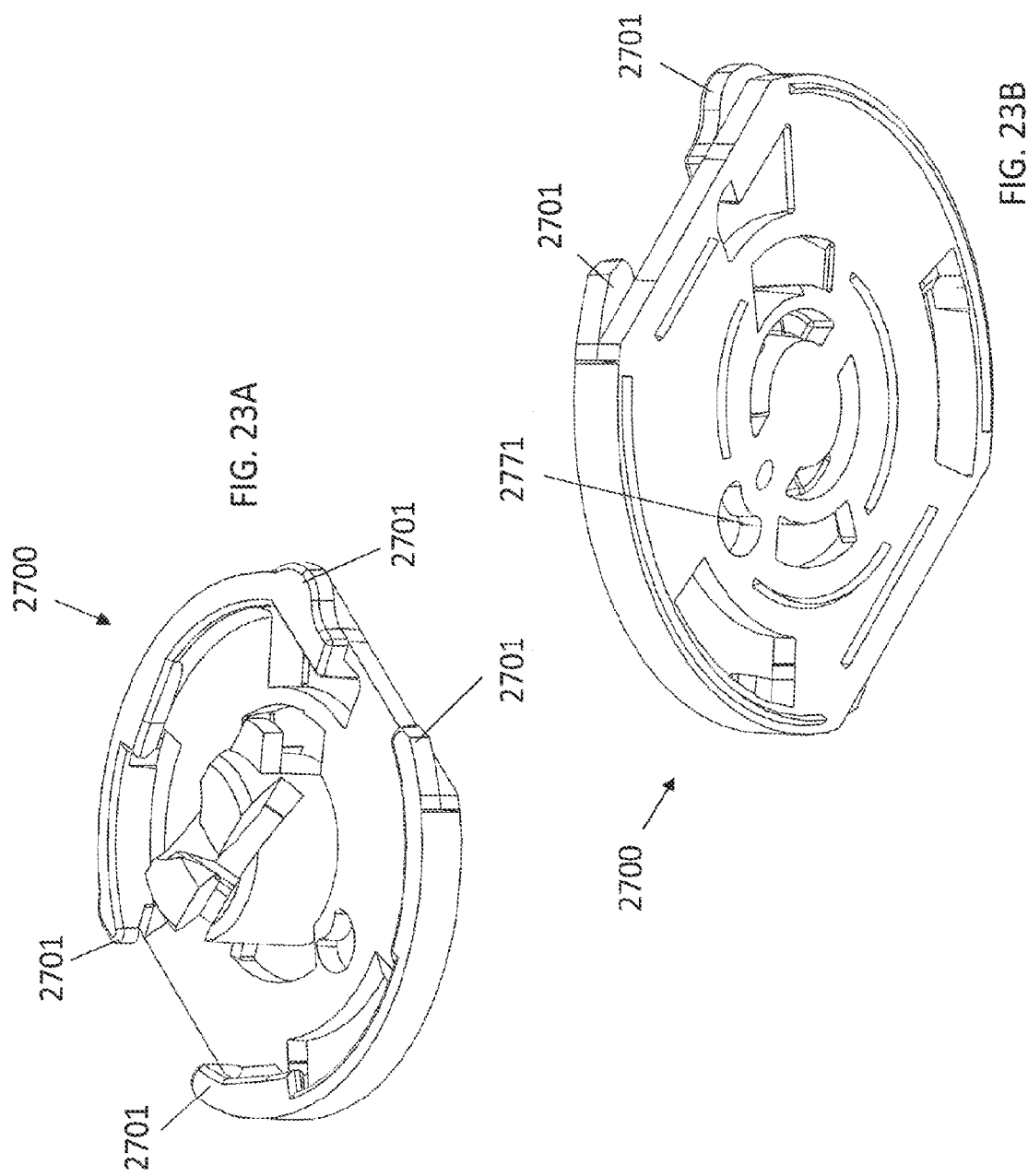

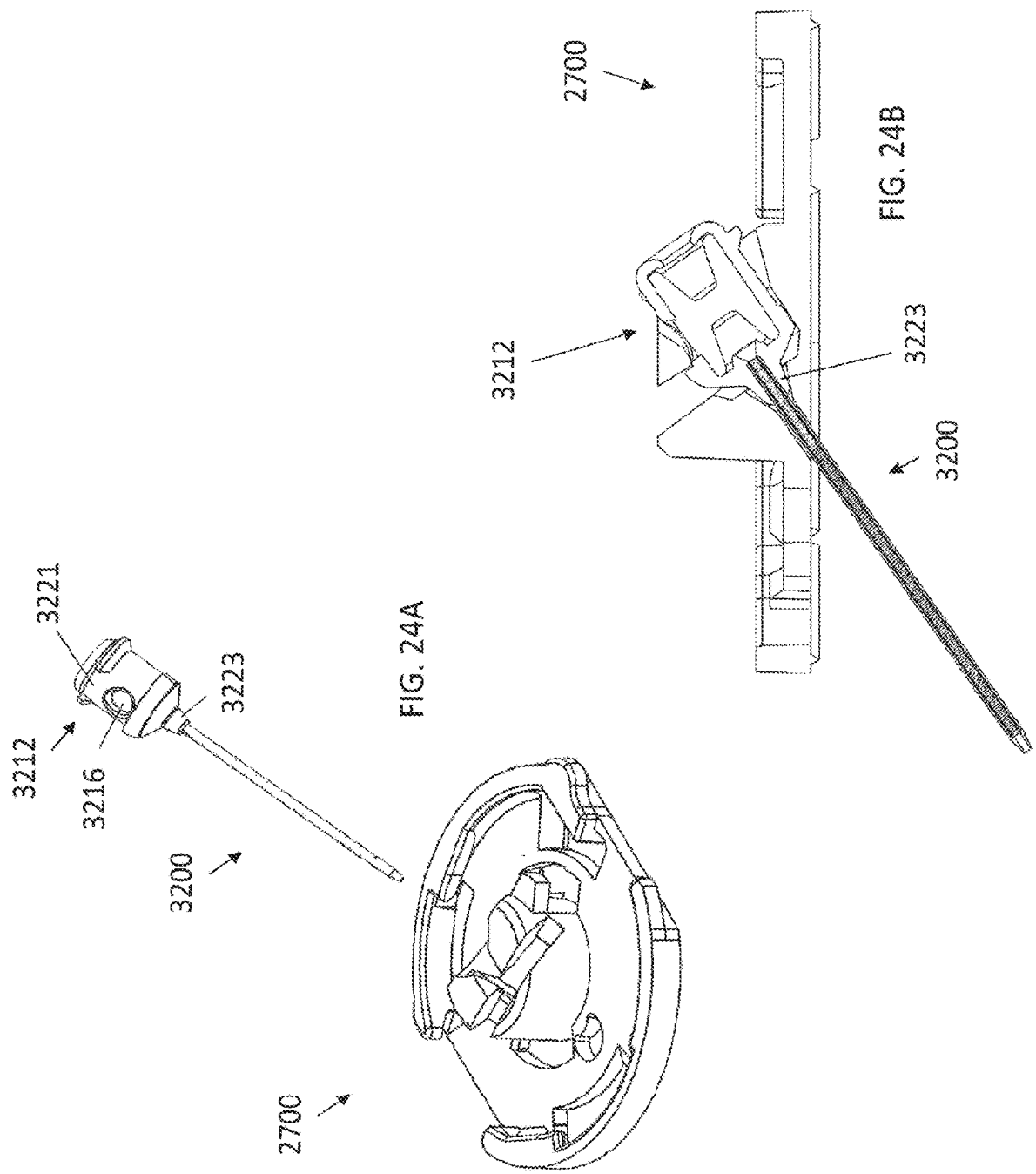

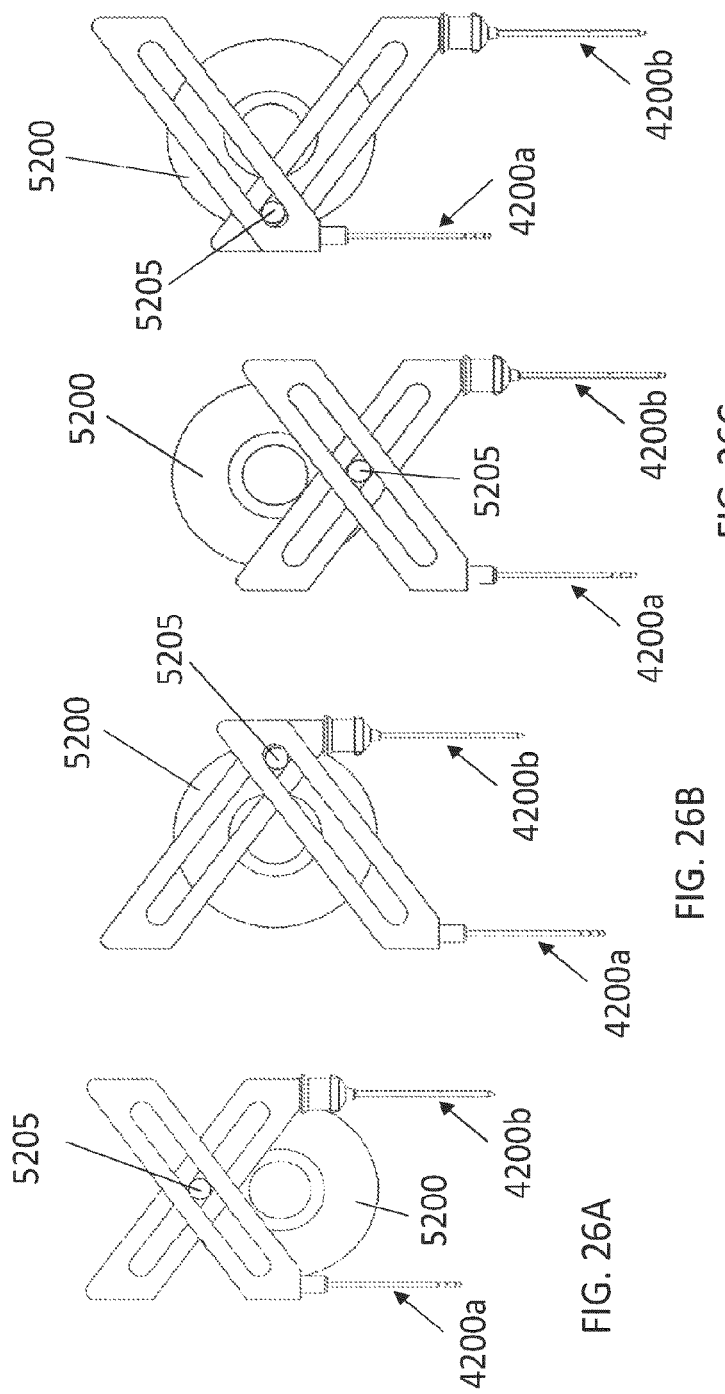

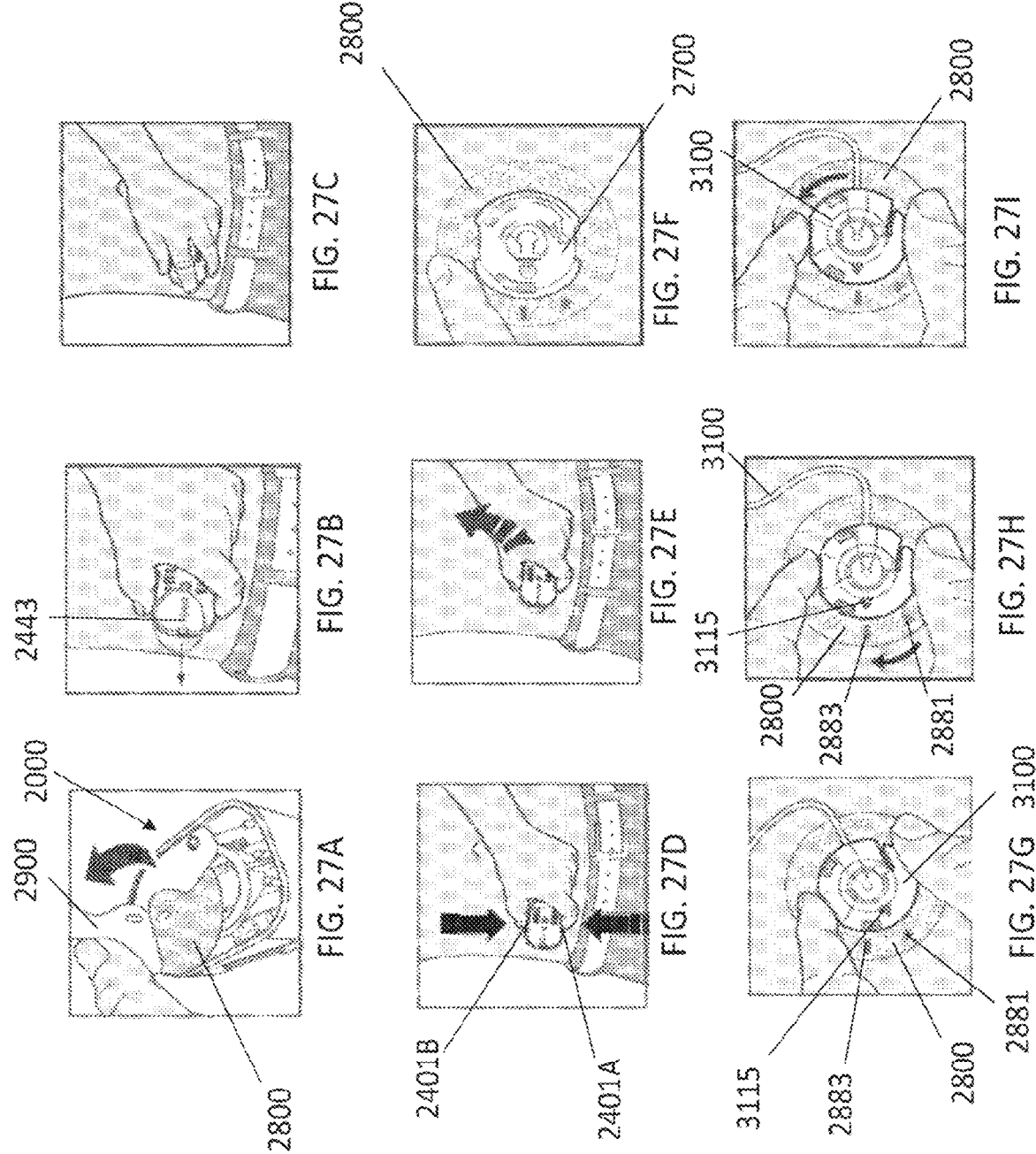

LINEAR INSERTION DEVICE WITH ROTATIONAL DRIVE

CROSS-REFERENCE TO RELATED APPLICATIONS

This application claims priority to U.S. Provisional Application No. 62/757,684, filed Nov. 8, 2018 and titled "Linear Insertion Device with Rotational Drive," the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

During drug delivery, it is often desirable to bypass the digestive system of a patient to avoid degradation of the drug's active ingredients that can be caused by the catalytic enzymes in the digestive tract and liver. Delivery of a drug other than by way of the intestines is known as parenteral delivery. Parenteral delivery of drugs in liquid form is often desired to enhance the effect of the substance being delivered, ensuring that the unaltered medicine reaches its intended sits at a significant concentration. Moreover, undesired effects associated with other routes of delivery, such as systemic toxicity, can potentially be voided by parenteral delivery. Further, many medicines are only available in liquid form, and/or the liquid may have desirable characteristics that cannot be achieved with solid or pill form.

Ambulatory infusion pumps have been developed for delivering liquid medicaments to a patient transdermally. These infusion devices have the ability to offer sophisticated fluid delivery profiles that can provide bolus delivery, continuous infusion, and variable flow rate delivery. Infusion of fluid from ambulatory infusion pumps, however, can be problematic, as the user is generally forced to choose between an infusion set with a soft delivery cannula, which tends to have high initial failure rates and is prone to kinking, or a steel needle set, which has a lower initial failure rate but is associated with increased pain and shortened time of use. Additionally, the challenge with current infusion sets is that the 90-degree (i.e., rigid cannula) infusion sets, which are easiest to insert, are also associated with the highest rates of failure, partially due to needle breakage and/or fluid leaking out of the relatively short insertion path. Infusion sets with a soft cannula, however, tend to be harder to insert and/or are associated with increased apprehension or intimidation. Additionally, when a needle is used to introduce the cannula of the infusion device into the subcutaneous layer of skin, there is a risk associated with inadvertent exposure to the needle. Further, patients may react adversely to viewing the needle prior to insertion and may, for example, be reluctant to place the needle into the skin. Other issues of concern in the design and use of transdermal insertion devices include ease of use by the patient and sterilization.

Accordingly, an infusion set (e.g., for use with an ambulatory infusion pump) that is efficient, safe, effective, and easy to insert into a patient is desired.

SUMMARY

In general, in one embodiment, a system for delivering fluid to a user transcutaneously includes a torsion spring, a drive wheel, a linear slide having a stylet attached thereto, and a cannula. The torsion spring, when actuated, is configured to rotate the drive wheel to cause the linear slide to move axially to drive the stylet and cannula into a user's skin.

This and other embodiments can include one or more of the following features. The drive wheel can be configured to rotate a first amount to axially drive the infusion cannula into the user's skin with a stylet, and the drive wheel can be configured to rotate a second additional amount to retract the stylet from the user's skin. The first amount can be approximately 180 degrees. The second additional amount can be approximately 180 degrees. The torsion spring can be configured to supply all energy required to both drive the infusion cannula and retract the stylet. The torsion spring, drive wheel, linear slide, and cannula can all be configured to be housed within an inserter housing prior to insertion of the stylet and cannula into the user's skin. The stylet and cannula can extend out of the housing for insertion into the user's skin. An infusion set base can be configured to removably couple to the inserter housing, and the infusion set base can be configured to attach to the user's skin. The infusion set base can include an adhesive on at least one surface thereof configured to attach the infusion set base to the user's skin. The infusion set base can be configured to engage with the cannula as the cannula is driven into the user's skin so as to hold the cannula in the user's skin as the stylet is retracted. The inserter assembly can include an automatic release mechanism configured to decouple the inserter from the infusion set base. The automatic release mechanism can include a post configured to engage with the linear slide as the linear slide moves axially, and the infusion set base can be configured to decouple from the inserter as the linear slide moves the post. The automatic release mechanism can include a plurality of arms configured to engage with the infusion set base to hold the infusion set base to the inserter prior to activation of the automatic release mechanism. The cannula can be flexible. A housing can be configured to house the torsion spring, drive wheel, linear slide, and cannula. The housing can include an angled surface therein upon which the drive wheel is rotational mounted so as to enable angled delivery of the stylet and cannula into the user's skin. The cannula can further include a septum at the proximal end thereof. The septum can be configured to seal upon removal of the stylet from the cannula. A fluid connection assembly can be configured to fluidically connect the cannula to a source of delivery fluid through the septum. The drive wheel can include a pin, and the linear slide can include a framework having an elongate slot therein. The elongate slot can be configured to be positioned around the pin to transfer rotational movement of the drive wheel to axial movement of the linear slide. The framework can include a curved portion extending radially outwards therefrom. The stylet can attach to the curved portion. The rotation of the pin through the curved portion can create a dwell in movement of the linear slide.

In general, in one embodiment, a system for delivering fluid to a user transcutaneously includes a cannula and an infusion set base. The cannula includes a barrel and an elongate flexible member. The barrel further includes a septum therein. The septum is configured to allow passage of a stylet through the cannula and to self-seal as the stylet is removed from the cannula. The infusion set base includes a central port through which the elongate flexible member is configured to extend, and the infusion set base is configured to lock the barrel thereto.

This and other embodiments can include one or more of the following features. An inserter can be configured to removably couple with the infusion set base. The inserter can be further configured to insert the cannula into the infusion set base. The inserter can be further configured to retract the stylet from the cannula. The infusion set base can further include one or more clips configured to open radially to allow the elongate flexible member to pass therethrough and to close radially around the barrel to lock the barrel thereto. The system can further include an inserter including a drive wheel and a linear slide. The drive wheel can be configured to rotate to cause the linear slide to move axially to drive the cannula into a user's skin. The drive wheel can include a pin, and the linear slide can include a framework having an elongate slot therein. The elongate slot can be configured to be positioned around the pin to transfer rotational movement of the drive wheel to axial movement of the linear slide. The framework can include a curved portion extending radially outwards therefrom. The stylet can be attached to the curved portion. Rotation of the pin through the curved portion can create a dwell in movement of the linear slide so as to allow time for the infusion set base to lock to the barrel. An infusion set cap can be configured to interlock with the infusion set base. The infusion set cap can include a needle configured to pierce the septum as the infusion set cap and infusion set base are mated. The needle can be configured to pierce the septum at a different angle than the stylet. The needle can be configured to pierce the septum at approximately a 10-65° degree angle relative to the stylet. The septum can include an elastomer. The barrel can compress the septum radially and axially. The septum can include a cylindrical outer wall and an H-shaped longitudinal cross-section.

In general, in one embodiment, a system for delivering fluid to a user transcutaneously, the system includes a torsion spring, a drive wheel, a first elongate body, and a second elongate body. The torsion spring, when actuated, is configured to rotate the drive wheel to drive the first elongate body and the second elongate body into a user's skin.

This and other embodiments can include one or more of the following features. The linear slide can be removably attached to the first elongate body and can be configured to move axially as the drive wheel rotates to drive the first elongate body into the user's skin. A second linear slide can be removably attached to the second elongate body and can be configured to move axially as the drive wheel rotates to drive the second elongate body into the user's skin. The first elongate body can be configured to provide fluid therethrough. The second elongate body can include a sensor thereon.

In general, in one embodiment, a method of delivering fluid transcutaneously to a patient, includes: (1) adhering an infusion assembly to skin of the patient, the infusion assembly including an inserter and an infusion set base, (2) activating a trigger on the inserter to insert a cannula subcutaneous tissue of the patient, the cannula supported after insertion by the infusion set base, (3) removing the inserter from the infusion set base so that the infusion set base remains adhered to the skin, (4) attaching a cap with tubing to the infusion set base, and (5) providing fluid to the tubing so that it travels through the cannula to the subcutaneous tissue of the patient.

In general, in one embodiment, a method of delivering fluid transcutaneously to a patient, includes: (1) adhering an infusion assembly to skin of the patient, the infusion assembly including an inserter and an infusion set base, (2) activating a trigger on the inserter to insert a cannula subcutaneous tissue of the patient, the cannula supported after insertion by the infusion set base, (3) removing the inserter from the infusion set base so that the infusion set base remains adhered to the skin, (4) attaching an insulin delivery device to the infusion set base, and (4) delivering insulin from the insulin delivery device so that it travels through the cannula to the subcutaneous tissue of the patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a top perspective view of an inserter and infusion set system.

FIG. 1B is an exploded view of the inserter and infusion set system of FIG. 1A.

FIG. 4B is a bottom view of a drive wheel having a plurality of curved linear slides attached thereto.

FIG. 6A is a top perspective view of the bottom housing of the system of FIGS. 1A-1B.

FIG. 8C is a top perspective view of the infusion set base and cannula of the system of FIGS. 1A-1B.

FIG. 8D is a side cross-section of the infusion set base of the system of FIGS. 1A-1B with the cannula inserted into the infusion set base.

FIGS. 10A-10E are simplified bottom views of the drive wheel and linear slide of the system of FIGS. 1A-1B as the drive wheel rotates to move the linear slide axially.

FIGS. 11A-11G are simplified bottom views of the drive wheel and linear slide of the system of FIGS. 16A-16B as the drive wheel rotates to move the linear slide axially.

FIGS. 12A-12B show linear compression springs that can be used to drive a linear slide for an infusion system.

FIG. 15A is cross-sectional view of the barrel of the cannula of the system of FIGS. 1A-1B with the stylet extending through the septum.

FIG. 15B is a cross-sectional view of the barrel of the cannula of the system of FIGS. 1A-1B with the needle of an infusion set cap extending through the septum (the rest of the cap is removed for clarity).

FIG. 16A is a top perspective view of another inserter and infusion set system.

FIG. 16B is an exploded view of the inserter and infusion set system of FIG. 16A.

FIG. 17A is a top perspective view of the drive wheel of the system of FIGS. 16A-16C.

FIG. 17B is a top perspective view of the drive wheel of the system of FIGS. 16A-16C without the torsion spring for clarity.

FIG. 17C is a bottom perspective view of the drive wheel of the system of FIGS. 16A-16C.

FIG. 18A is a top perspective view of the linear slide of the system of FIGS. 16A-16C.

FIG. 18B is a top view of the linear slide of the system of FIGS. 16A-16C.

FIG. 19A is a top perspective view of the top housing of the system of FIGS. 16A-16C.

FIG. 19B is a bottom perspective view of the top housing of the system of FIGS. 16A-16C.

FIG. 21A is a top perspective view of the bottom housing of the system of FIGS. 16A-16C.

FIG. 21B is a bottom view of the bottom housing of the system of FIGS. 16A-16C.

FIG. 22A is a top perspective view of the locking mechanism of the system of FIGS. 16A-16C.

FIG. 22B is a bottom perspective view of the locking mechanism of the system of FIGS. 16A-16C.

FIG. 23A is a top perspective view of the infusion set base of the system of FIGS. 16A-16C.

FIG. 23B is a bottom perspective view of the infusion set base of the system of FIGS. 16A-16C.

FIG. 24A is a top perspective view of the infusion set base and cannula of the system of FIGS. 16A-16C.

FIG. 24B is a side cross-section of the infusion set base of the system of FIGS. 16A-16C with the cannula inserted into the infusion set base.

FIGS. 26A-D are simplified views of the drive wheel and linear slide for a system that is configured to insert multiple cannulas.

FIGS. 27A-27I show exemplary steps for inserting a cannula with an inserter.

DETAILED DESCRIPTION

Figure 2A:
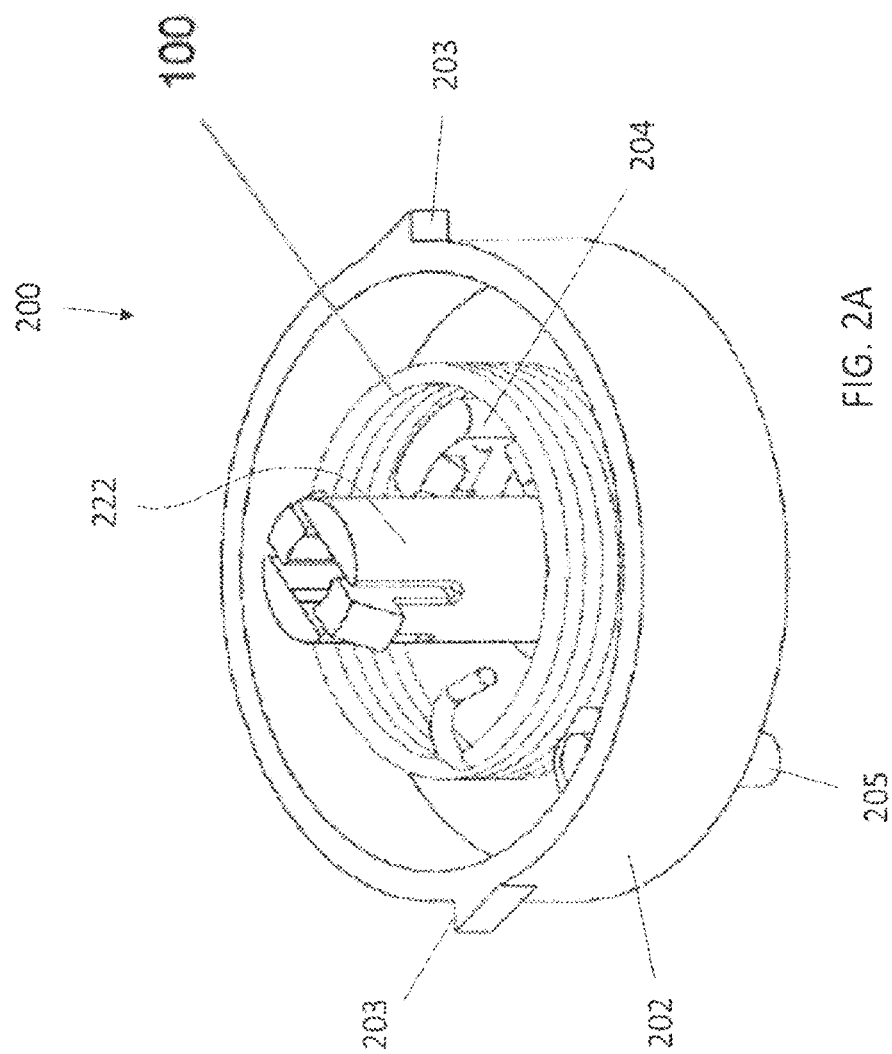
FIG. 2A is a top perspective view of the drive wheel of the system of FIGS. 1A-1B.

Described herein is an infusion set and inserter that is advantageously easy to use, comfortable, and durable. The inserter can be removably attached to the infusion set so as to allow the user to affix the infusion set to the skin, actuate the inserter, and remove the inserter to leave the cannula in the subcutaneous tissue and the infusion set attached to the skin. The stylet used to introduce the cannula can be retracted into the inserter body during the insertion cycle for safe storage and disposal.

Referring to FIGS. 1A and 1B, an exemplary inserter and infusion set system 1000 includes a top housing 400, a torsion spring 100, a drive wheel 200, a linear slide 300 with a stylet 1300, a bottom housing 500, a lock ring 600, an infusion set base 700, an adhesive patch 800 to adhere the infusion set base 700 to the user, and an adhesive liner 900 that can be removed to expose the adhesive patch 800. The inserter (top housing 400, torsion spring 100, drive wheel 200, linear slide 300, bottom housing 500, and lock ring 600) can be used to insert a cannula 1200 and adhere the infusion set base 700 to the user, e.g., for infusion of fluid or medicament, such as insulin, to the patient.

Figure 2B:
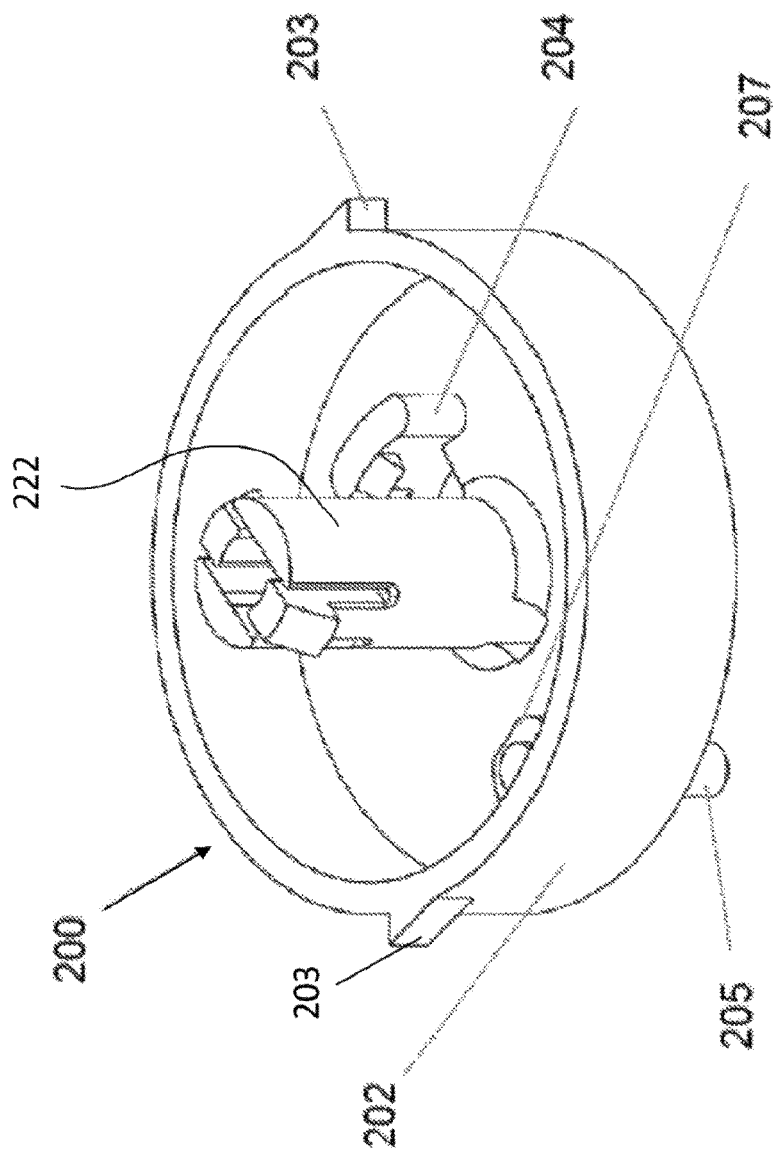
FIG. 2B is a top perspective view of the drive wheel of the system of FIGS. 1A-1B without the torsion spring for clarity.
Figure 2C:
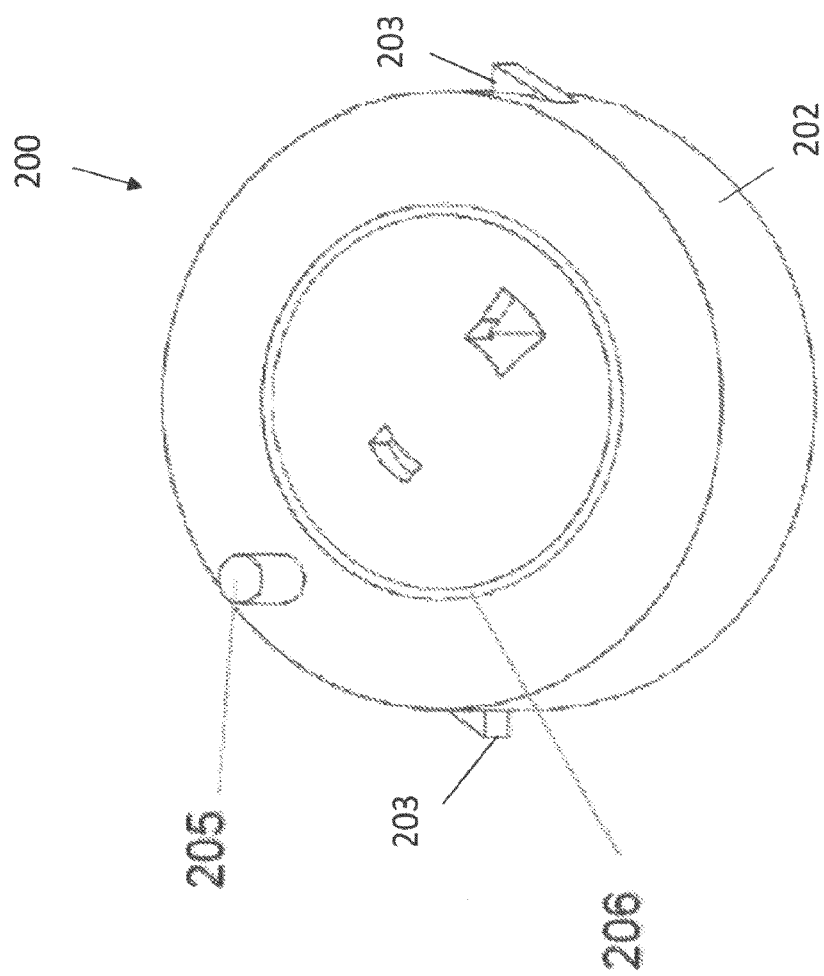
FIG. 2C is a bottom perspective view of the drive wheel of the system of FIGS. 1A-1B.

Referring to FIGS. 2A-2C, the drive wheel 200 can be a circular disc with a circumferential edge or rim 202. The drive wheel 200 can be made from an engineering polymer such as polycarbonate, ABS, nylon, or polyurethane. The drive wheel 200 can include a torsion spring 100 that is wound (energized) to a point where, upon release, the total travel is mechanically translated, to rotate the drive wheel 200 (and release the cannula 1200 into the subcutaneous tissue). The torsion spring 100 can be a multi-wind round wire or a multi-wind flat (rectangular wire). Exemplary torsion springs and drive wheels are described in International Patent Application No. PCT/US2018/025712, filed Apr. 2, 2018, now International Publication No. WO 2018/184012, the entirety of which is incorporated by reference herein. The torsion spring 100 can have design features (e.g., hooks) on the ends thereof to capture and/or engage with the drive wheel 200 (e.g., with post 204) and the top housing 400 (e.g., post 403) so as to fix the ends of the torsion spring 100 to deliver spring force when actuated. The drive wheel 200 can include additional mass at or near the radial edge of the wheel 200 to increase the rotational inertia of the drive wheel 200. This mass can include the continuous rim 202 and/or multiple partial walls/rims. Further, the drive wheel 200 can include a shaft 222 configured to engage with the upper housing 400 to enable rotation of the drive wheel 200. Additionally, the drive wheel 200 can include one or more external ramps 203 configured to interact with a control 401 (described below) so as to prevent rotation of the drive wheel 200 until activated. Further, the drive wheel 200 can include a pin 205 to provide engagement with the linear slide 300. The pin 205 can be normal to the wheel surface and can have sufficient length to engage the linear slide 300. Other mechanical features that can be used for engagement with the linear slide include rods, slots, holes, teeth, or ramps. The drive wheel can further include a boss 206 or other feature to provide friction reduction during rotational energy transfer to the linear slide 300.

Figure 3A:
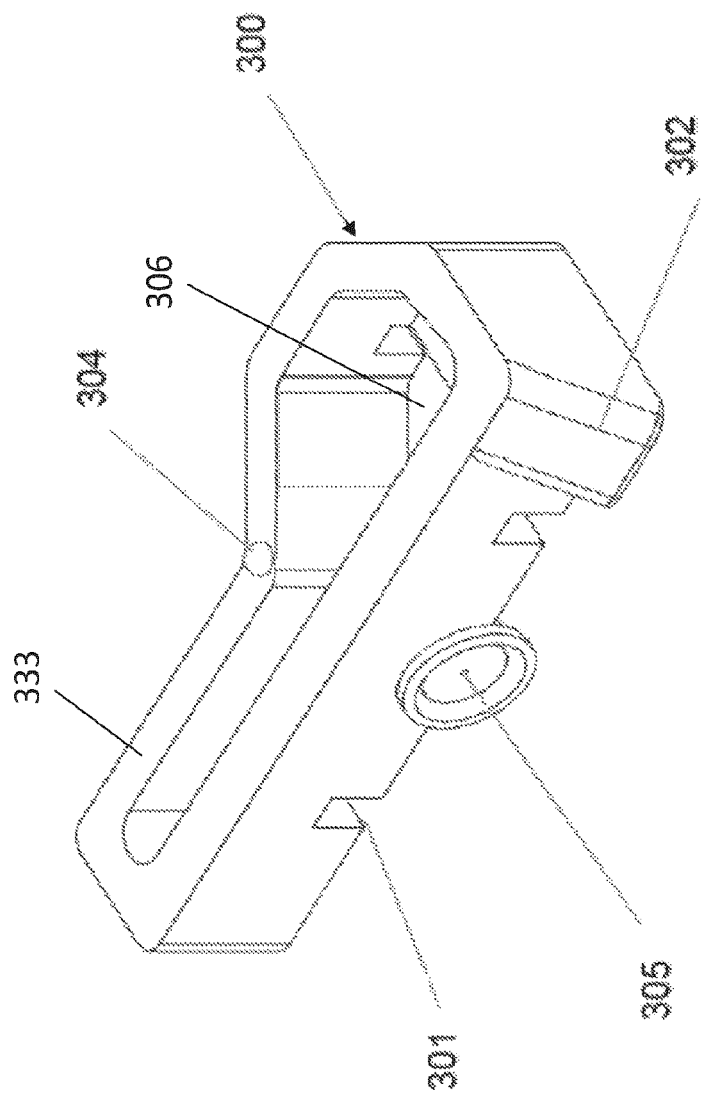
FIG. 3A is a top perspective view of the linear slide of the system of FIGS. 1A-1B.
Figure 3B:
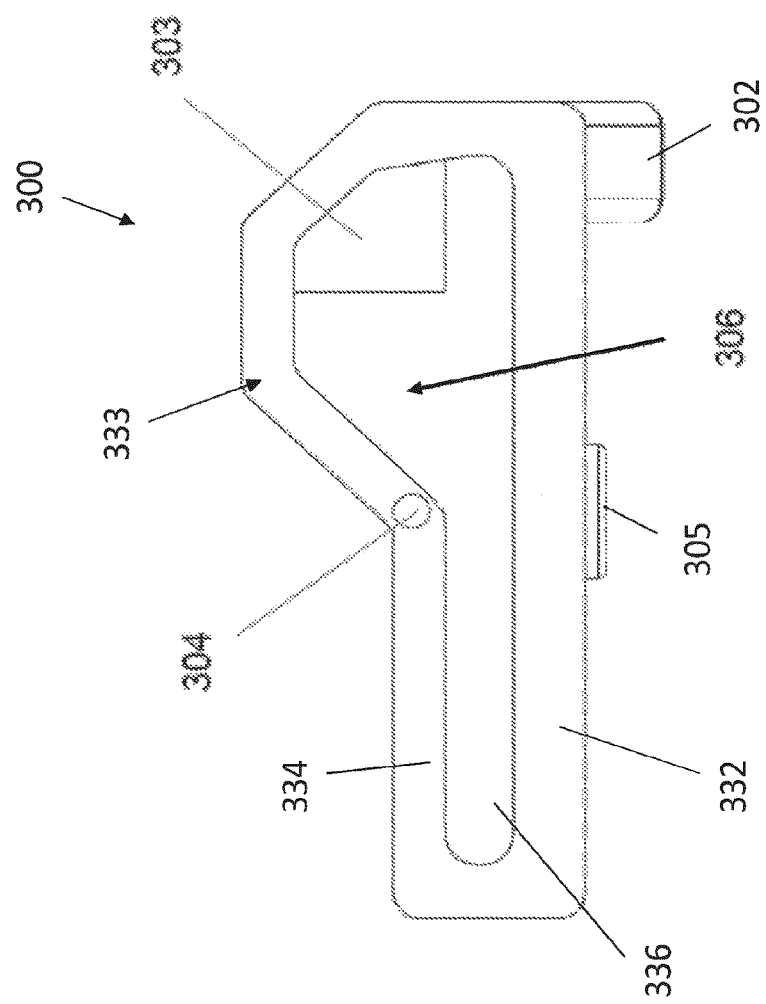
FIG. 3B is a top view of the linear slide of the system of FIGS. 1A-1B.

Referring to FIGS. 3A-3B, the linear slide 300 can include an outer framework 333 with a central elongate slot 306 therein and a port 305 for attachment of the stylet 1300 (see FIG. 1B). The slot 306 is configured to be positioned over the pin 205 of the drive wheel 200. The framework 333 and corresponding slot 306 can be curved and/or straight. For example, referring to FIG. 3B, the framework 333 can be straight on a first side 332 (i.e., the side attached to the stylet 1300 via port 305) while the opposite side 334 can have a straight section and a curved section (i.e., curved radially outwards) so as to form a substantially straight portion 336 of the slot 306 and a bulbous portion 303 of the slot 306, respectively. The asymmetric nature of the slide 300 can be configured to control speed of travel of the linear slide 300 and/or to limit or stop travel to control the direction of the linear slide 300, as described further herein. The linear slide 300 can further include a boss 304 on the top surface thereof to limit frictional contact with the drive wheel 200. Additionally, the linear slide 300 can include a plurality of rail engagement features 301 (e.g., slots, holes, teeth, ramps, or bosses) in the bottom surface of the outer framework 333 for sliding contact with the rails 504 of the bottom housing 500. As described further below, movement of the linear slide 300 along the pin 205 as the drive wheel 200 rotates will thus result in axial movement of the stylet 1300 along the rails 504 of the bottom housing 500, thereby resulting in insertion of the cannula 1200 into the tissue. Finally, the linear slide 300 can include an external ramp 302 configured to interact with the lock ring 600 to release the infusion set base, as described further below. The linear slide 300 can be made, for example, of a polymer such as polycarbonate, ABS, nylon, or polyurethane.

Figure 5A:
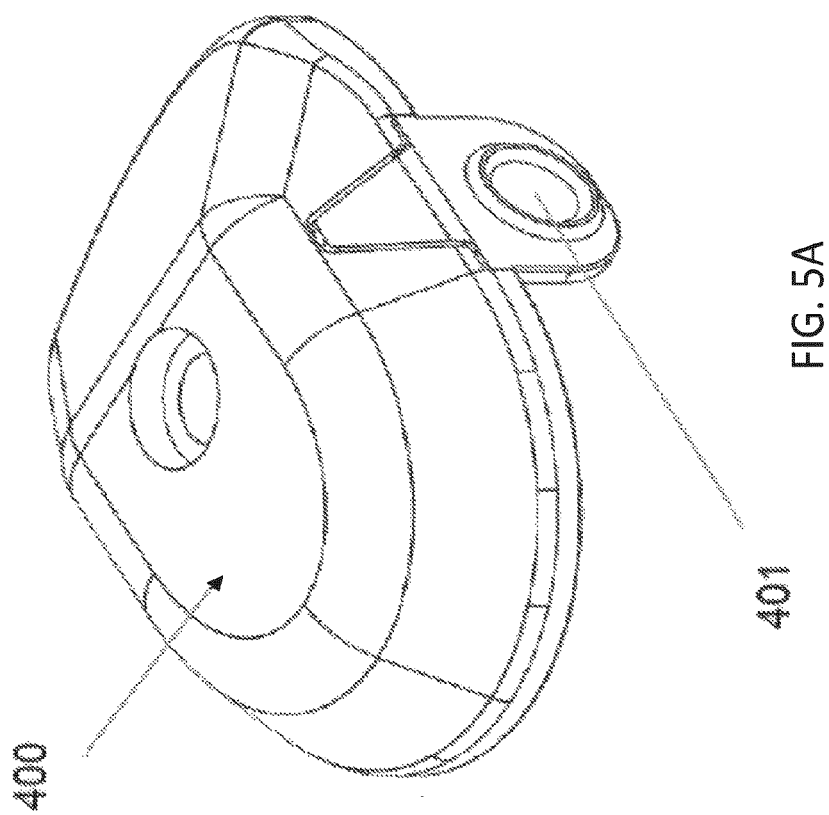
FIG. 5A is a top perspective view of the top housing of the system of FIGS. 1A-1B.
Figure 5B:
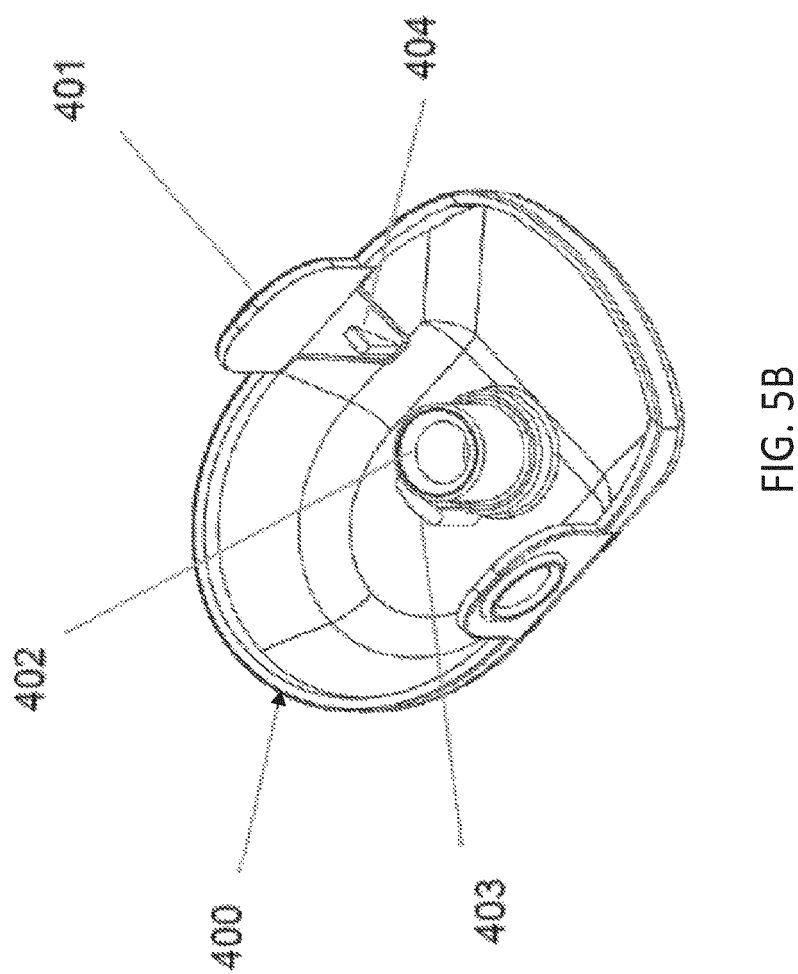
FIG. 5B is a bottom perspective view of the top housing of the system of FIGS. 1A-1B.

Referring to FIGS. 5A-5B, the top housing 400 can house the drive wheel 200 and linear slide 300. The top housing 400 and bottom housing 500 can make up the entire exterior body of the inserter and can be made, for example, from a polymer such as polycarbonate, ABS, nylon, or polyurethane. The top housing 400 can include an external shaft 402 for engagement with the central shaft 222 of the drive wheel 200 such that the drive wheel 200 can rotate within the external shaft 402 when activated. The top housing 400 can further include the post 403 configured to fix the end of the torsion spring 100. The top housing 400 can additionally include one or more user-accessible buttons 401 configured to release the cannula 1200 (e.g., insert the cannula 1200 and stylet 1300 into the subcutaneous tissue of the user) when activated by the user. That is, pushing the controls 401 can cause inner teeth 404 on the controls 401 to move up and away from the external ramps 203 on the drive wheel 200, thereby allowing the drive wheel 200 to rotate. In some embodiments, the control 401 can be integral to the top housing 400. In other embodiments, the control 401 can be a separate component that fits into the top housing 400 and protrudes above or remains flush with the surface thereof.

The activation of the control 401 can cause the torsion spring 100 rotate, which in turn can rotate the drive wheel 200 to cause the linear slide 300 to move axially to push the stylet 1300 and cannula 1200 into the subcutaneous tissue (e.g., an angle based upon the angled surface of the bottom housing 500 as described further below). An exemplary sequence of the drive wheel 200 (rotating counterclockwise) and linear slide 300 (moving axially along axis 1011) is shown in FIG. 10A-10E. At FIG. 10A, the drive wheel 200 is charged and locked into place (e.g., with the control 401), and the linear slide 300 is in the ready position. At FIG. 10B, the drive wheel 200 is unlocked (e.g., with the control 401) and rotates counterclockwise, which allows the drive wheel 200 to accelerate with no load (i.e., before the pin 205 comes into contact with the linear slide 300). At FIG. 10C, the drive wheel 200 continues rotating counterclockwise, and the linear slide 300 engages with the drive wheel 200 via pin 205. At FIG. 10D, the drive wheel 200 is rotated to the nadir (lowest) point, which in turns moves the linear slide 300 downwards for full insertion of the cannula (via attachment port 305). At FIG. 10E, the drive wheel is rotated further clockwise to a "stop" position, e.g., caused by interaction of the linear slide 300 with a stop 509 on the lower housing 500. The movement of the drive wheel 200 to the stop position moves the linear slide 300 back up axially into the completed position, thereby removing the stylet 1300 from the tissue and leaving the cannula 1200 in place. In some embodiments, the stylet 1300 can be retracted from the cannula 1200 such that it is drawn completely into the housing 400/500.

Figure 6B:
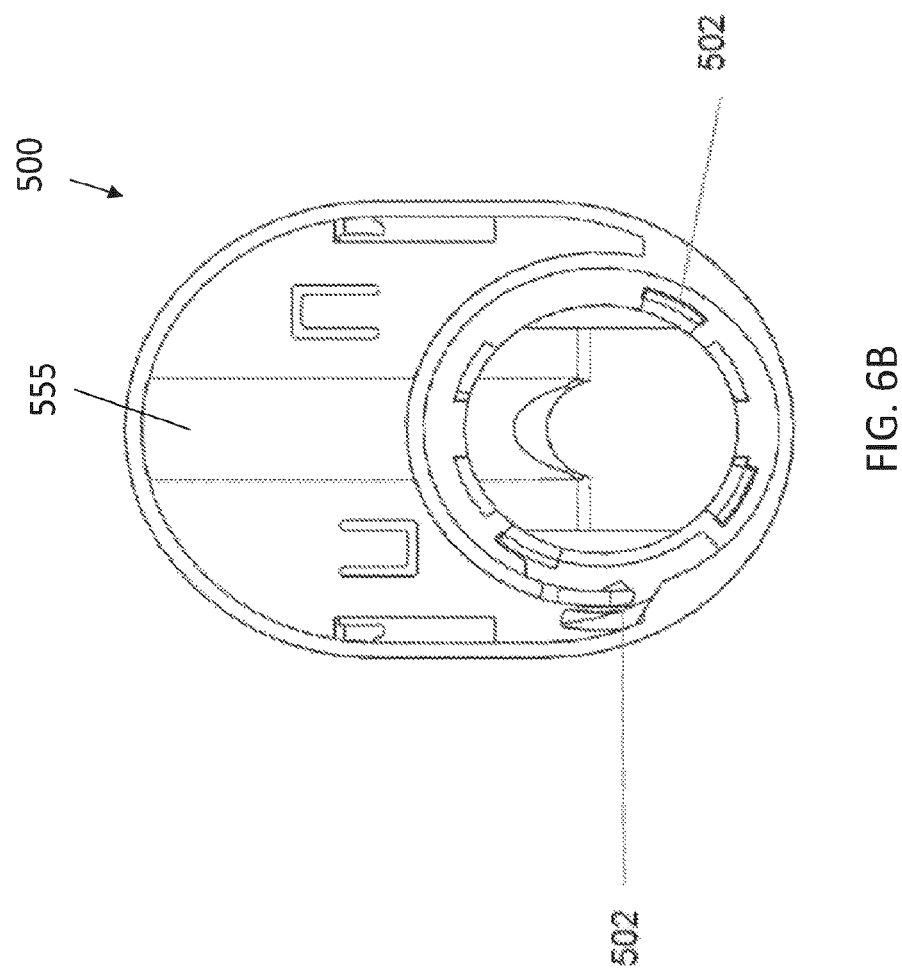
FIG. 6B is a bottom view of the bottom housing of the system of FIGS. 1A-1B.

Referring to FIGS. 6A-6B, the bottom housing 500 can include a slanted surface 551 and an opening 553 through which the cannula (attached to port 305 of the linear slide 300) can extend. The slanted surface 551 can extend at a 15°-45° angle relative to the bottom surface 555 of the bottom housing 500. The angle of the slanted surface 551 can set the angle of entry (and exit) for the stylet 1300 and cannula 1200 of between 0° and 45° relative to the bottom surface 555 and/or the surface of the patient's skin. The rails 504 can extend along the slanted surface 551 for engagement with the linear side 300 (i.e., the rails 504 can limit movement of the linear slide to the axial direction even as the drive wheel rotates). The underside of the bottom housing 500 can further include clips 502 for attachment or engagement with the lock ring 600. In some embodiments, the bottom housing 500 can include one or more features to increase durability. For example, slots in the bottom housing may allow more flexibility in the housing to absorb any outside forces that could act upon the device.

Figure 7A:
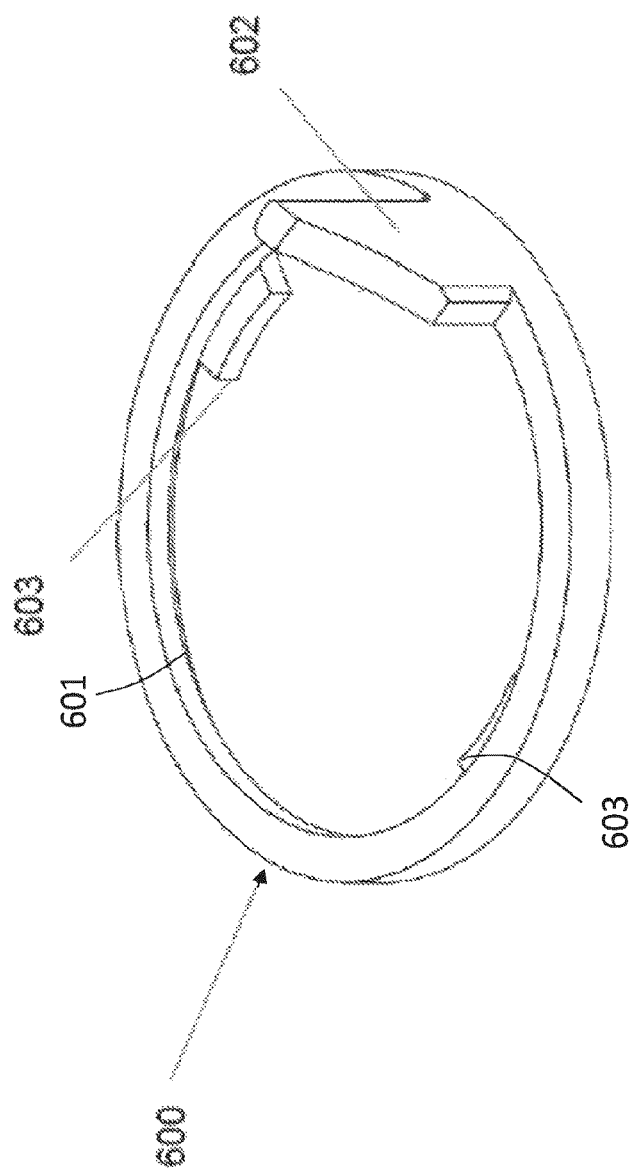
FIG. 7A is a top perspective view of the lock ring of the system of FIGS. 1A-1B.
Figure 7B:
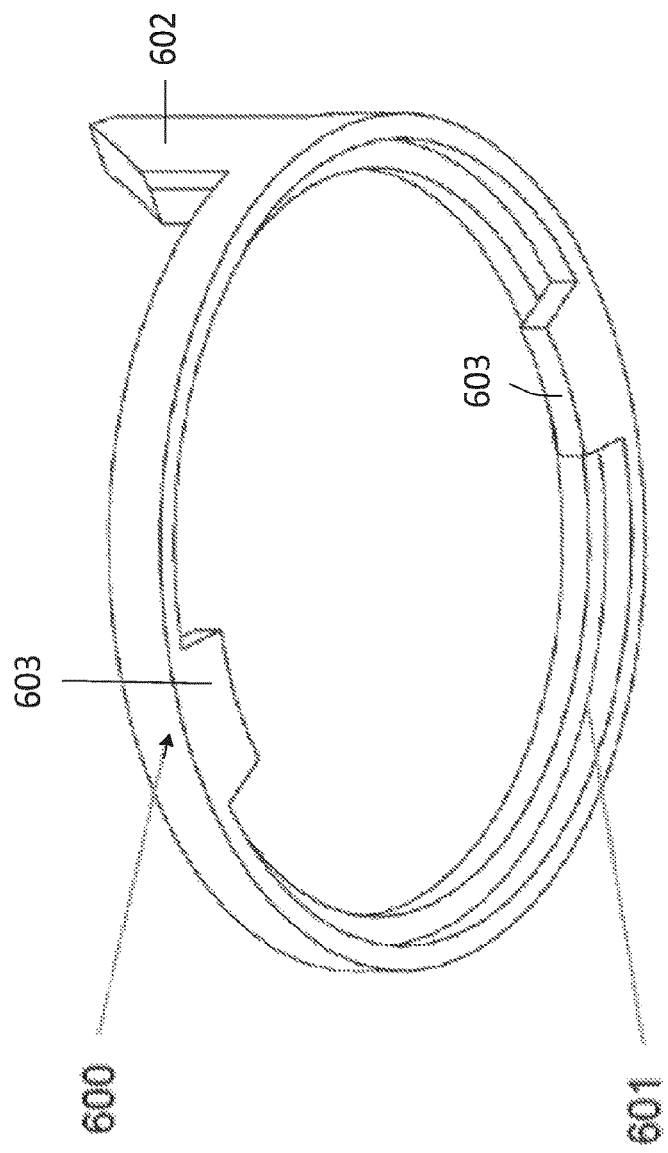
FIG. 7B is a bottom perspective view of the lock ring of the system of FIGS. 1A-1B.
Figure 8A:
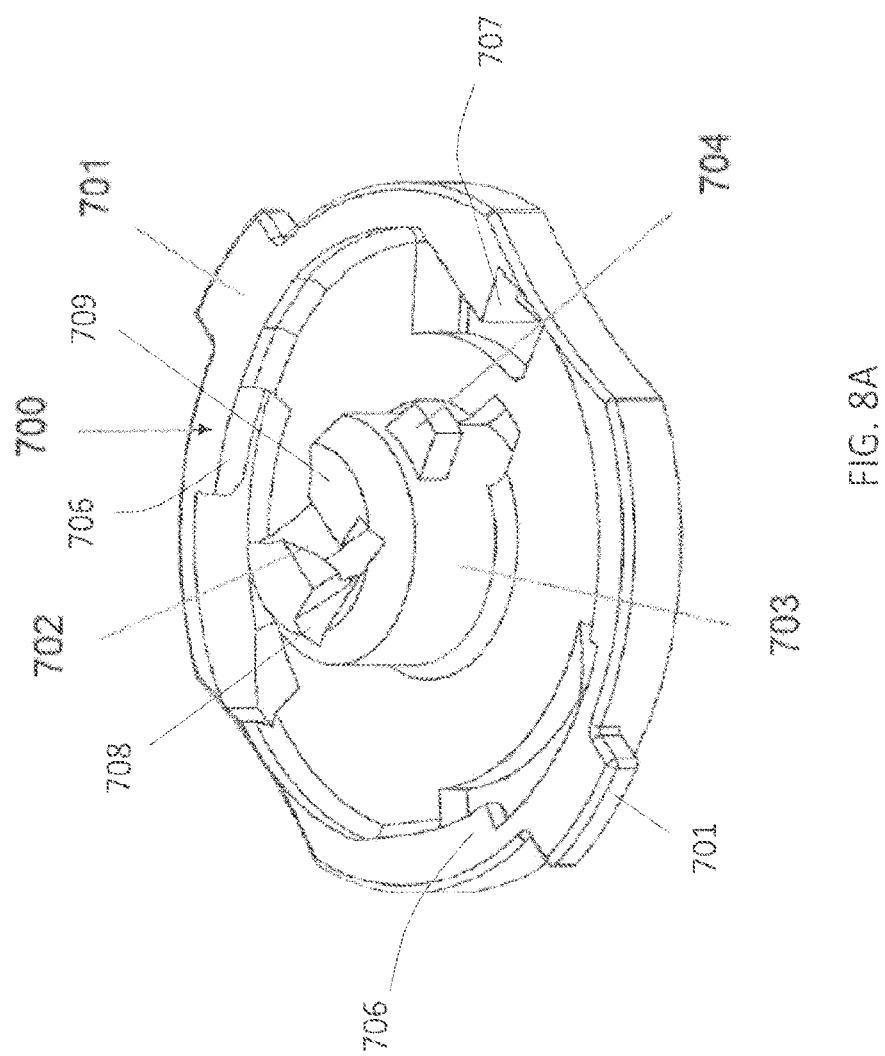
FIG. 8A is a top perspective view of the infusion set base of the system of FIGS. 1A-1B.
Figure 8B:
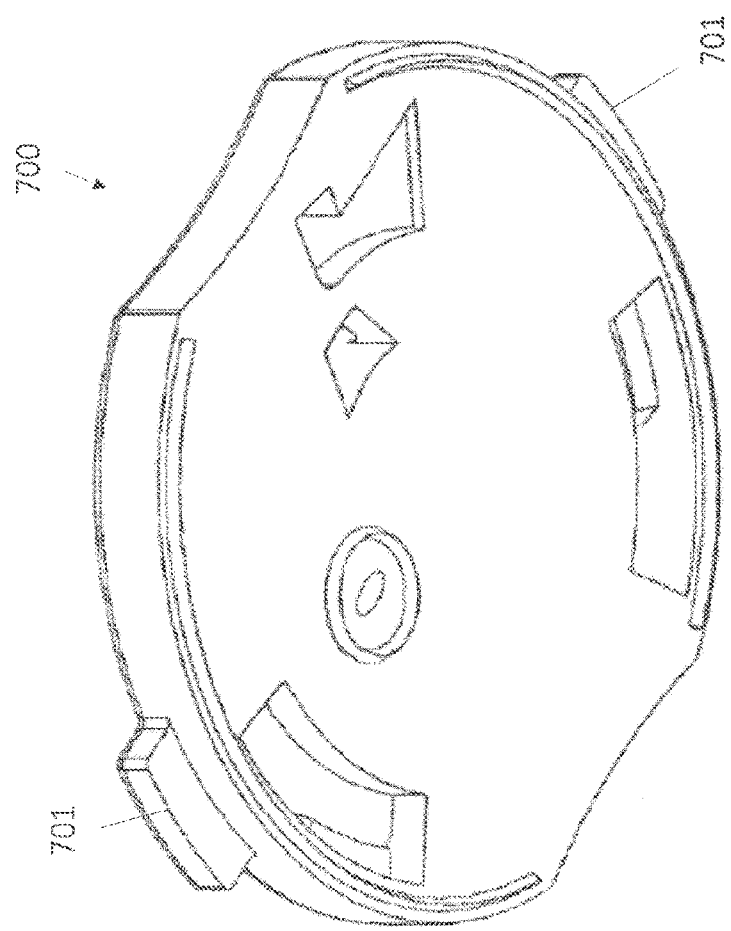
FIG. 8B is a bottom perspective view of the infusion set base of the system of FIGS. 1A-1B.

Referring to FIGS. 7A-7B, the lock ring 600 can be configured to hold the infusion set base 700 thereto during the insertion cycle and, when actuated by features on the linear slide 300, can release the infusion set base 700 therefrom at the completion of the cannula insertion cycle. The lock ring 600 can thus include a post 602. As the linear slide 300 moves axially downwards (i.e., as the cannula 1200 is being inserted), the external ramp 302 on the linear slide 300 can push the post 602, thereby causing the lock ring 600 to rotate slightly (e.g., 10-20 degrees). Rotating the lock ring 600 can cause internal tabs 603, which were positioned under (i.e., axially aligned with) external tabs 701 of the base 700, to rotate out of alignment with the external tabs 701, releasing the lock ring 600 and the rest of the inserter from the infusion set base 700. In some embodiments, the lock ring 600 can include a rail 601 for sliding engagement with the clips 502 of the bottom housing 500 (i.e., to hold the lock ring 600 to the bottom housing 500). The lock ring 600 can be made, for example, of a polymer such as polycarbonate, ABS, nylon, or polyurethane.

Figure 14:
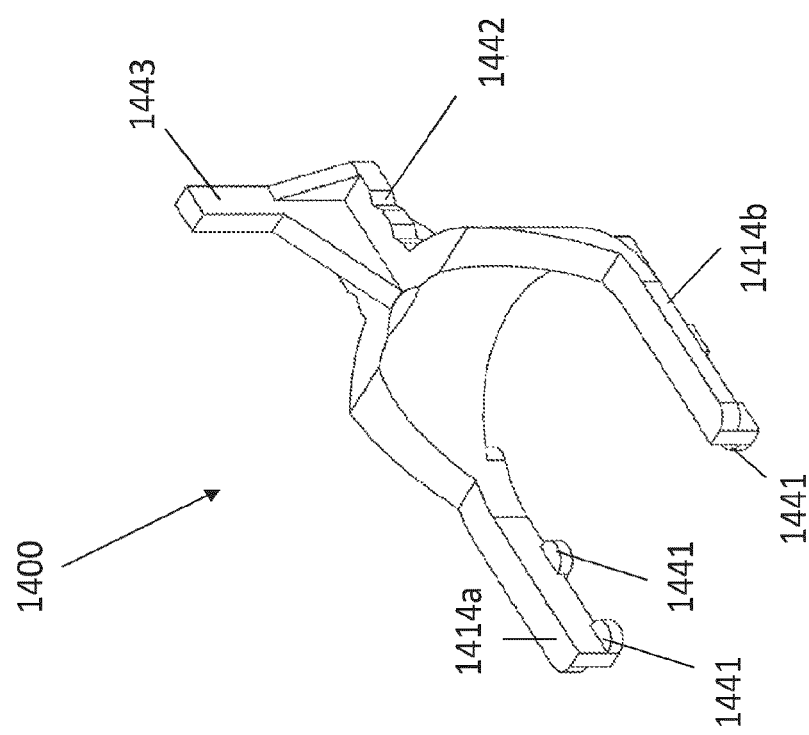
FIG. 14 is a top perspective view of an exemplary multiple arm locking mechanism that can be used to hold an infusion set base to an inserter.

Referring to FIG. 14, in some embodiments, the lock ring 600 can be replaced by a multiple arm locking mechanism 1400. The locking mechanism 1400 can have a tuning fork or horseshoe shape and can include a first arm 1414a and a second arm 1414b to hold the infusion set base 700 thereto via tabs 1441 that can be positioned underneath tabs or other features of the infusion set base 700. Further, the locking mechanism 1400 can include a post 1443 at the apex of the arms 1414a,b that extends axially upwards (e.g., up through the slanted surface 551 of the bottom housing 500) and alongside the drive wheel 200 and slider 300 opposite to the stylet 1300. As the drive wheel 200 moves to close to the final stop position, the slider 300 can hit the post 1443, causing the arms 1414*a,b* to move laterally backwards (in the direction of the post 1443), disengaging the tabs 1441 from the infusion set base 700 and releasing the infusion set base 700 from the inserter.

Referring to FIGS. 8A-8D, the infusion set base 700 can be configured to adhere to the skin of the patient (via adhesive patch 800). Further, the infusion set base 700 can be configured to engage with and hold the cannula 1200 after insertion of the cannula 1200 by the inserter (and after removal of the inserter upon release by the lock ring 600). Thus, the infusion set base 700 can include a central cannula port 703 through which the cannula 1200 can extend. Further, the port 703 can include clips 709 configured to engage with the proximal barrel 1212 of the cannula so as to lock it therein after insertion (even upon retraction of the stylet 1300). External tabs 701 can engage with the locking ring 600 to hold the infusion set base to the inserter until released. The infusion set base 700 can further include a post 704 extending radially from the port 703 and overhangs 706, which can all be configured to engage with the cap 1100 (see FIGS. 9A-9B) to hold the cap 1100 thereto. Further, a tooth 707 can act as a locking element to lock and release the cap 1100 therefrom, as described further below.

Referring still to FIGS. 8C-8D, the cannula 1200 used herein can include an elongate flexible member 1206 attached at its proximal end to a barrel 1212. The elongate flexible member 1206 can include a plurality of holes through the wall thereof that are positioned along an axial length and radially around the cannula, and the distal end of the flexible elongate member 1206 can be substantially atraumatic. Exemplary cannula elongate flexile members are described in International Patent Application No. PCT/US2018/025712, filed Apr. 2, 2018, now International Publication No. WO 2018/184012, the entirety of which is incorporated by reference herein. The barrel 1212 can include a side port 1216 and a distal port 1218. Additionally, the barrel 1212 can include a ledge 1219 therearound configured to engage with the clips 709 on the insertion base 700 to hold the cannula 1200 therein. Further, referring to FIGS. 15A-15B, the barrel 1212 can house a septum 1515 therein. The septum 1515 can be made, for example, of an elastomer such as silicone and can be compressed radially and axially within the barrel 1212. In some embodiments, the septum 1515 can include one or more coatings and/or material additives such as metal oxides. As shown in FIGS. 15A-15B, the septum 1515 can have a cylindrical outer wall with an H-shaped longitudinal cross-section (i.e., with bores at the proximal and distal ends of the barrel 1212). The septum 1515 can be configured to be punctured along the central axis of the barrel 1212 with the stylet 1300 (via distal port 1218), but can self-seal upon removal of the stylet 1300 from the cannula. Further, the septum 1515 can be configured to be punctured at an angle (e.g., 10°-75°, such as 10°-65° or 45°-75°) relative to the central axis of the barrel with a needle 888 (via side-port 1216) and can again self-seal if removed. In some embodiments, the cannula 1200 can be held at an angle (e.g., 15°-45°) relative to the bottom of the infusion set base 700 while the septum can puncture at a 45°-75° angle relative to the central axis of the cannula 1200 such that the needle 888 inserts into the septum 1515 at a 90° angle (perpendicular) to the bottom of the infusion set base 700 (i.e., to the user's skins). The needle 999 can be part of an infusion cap 1100, as described further below. The septum 1515 can thus be punctured at multiple angles and/or multiple times without degradation of the fluid path therethrough The septum 1515 can further be multifunctional, as it can be used as a friction fit for the holding the cannula 1200 onto the stylet 1300 (until the stylet 1300 is actively retracted) as well as a transfer point between the cannula 1200 and fluid from the needle 888. Further, the septum 1515 can be pierced by a number of different types of needles, including solid needles, hollow needles, or hypodermic needles.

Figure 9A:
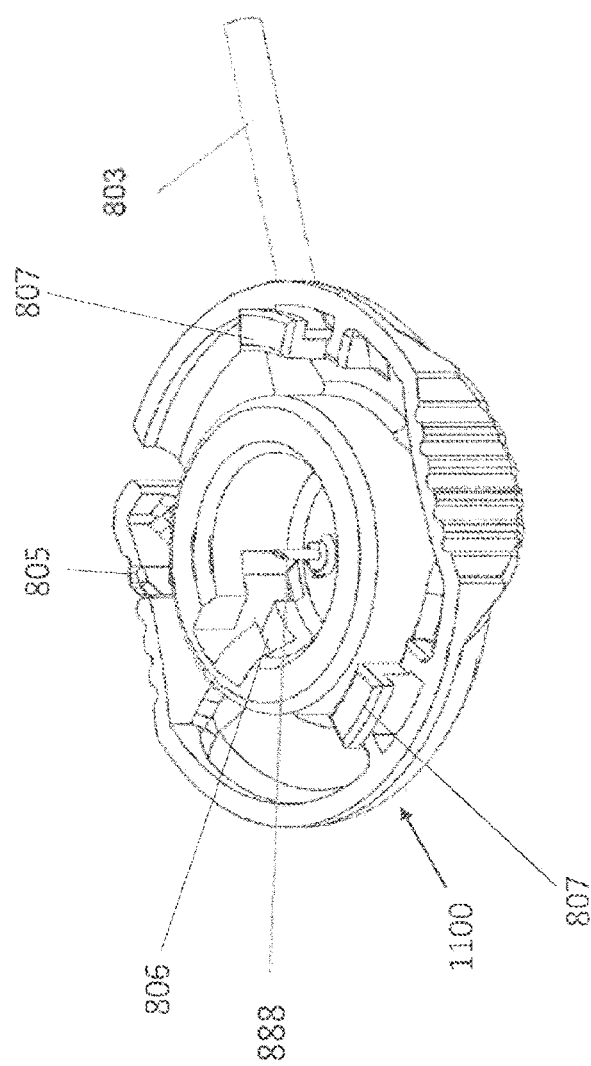
FIG. 9A is a bottom perspective view of an infusion set cap for use with the system of FIGS. 1A-1B.
Figure 9B:
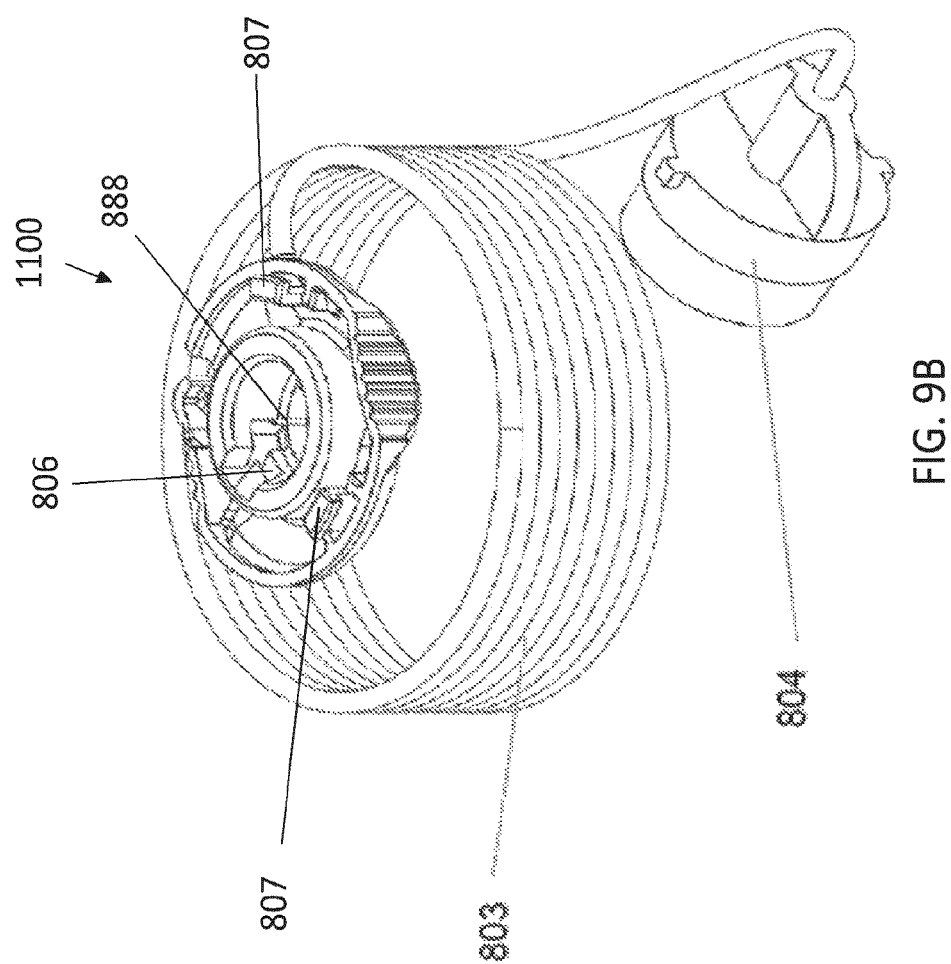
FIG. 9B is a bottom perspective view of an infusion set cap and tubing for use with the system of FIGS. 1A-1B.
Figure 11G:
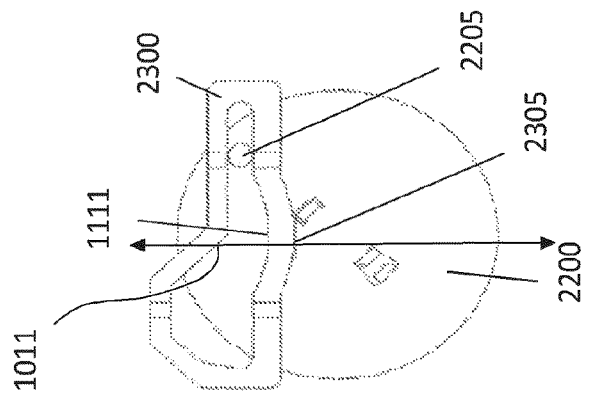
Figure 11F:
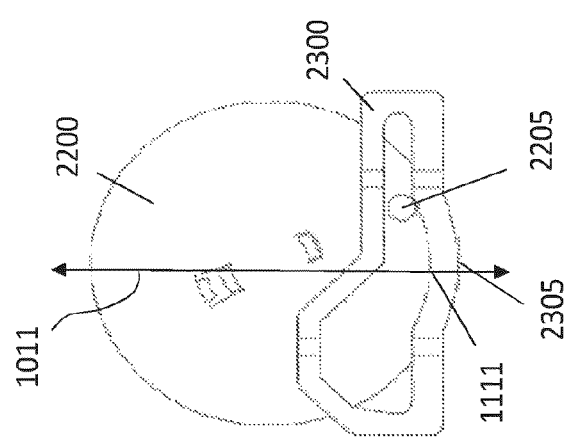
Figure 11E:
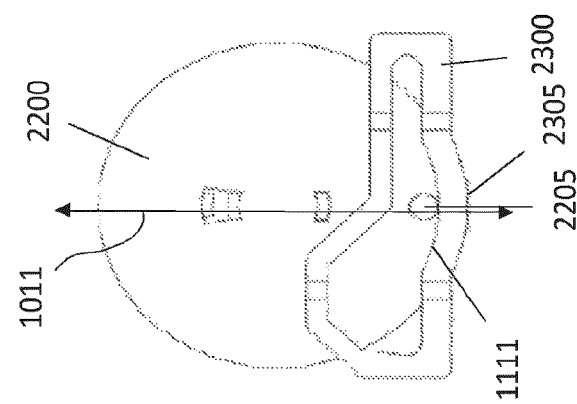

Referring to FIGS. 9A-9B, the infusion set cap 1100 can include the needle 888 and can be configured to attach to and be placed over the infusion set base 700 for delivery of fluid (e.g., insulin) to the subcutaneous tissue of the user. The infusion set cap 1100 can further include a fluid tubing 803 and pump connector 804 for transfer of the fluid from the pump. The infusion set cap 1100 can be held to the infusion set base 700, for example, with a shelf 806 (configured to house post 704) and hooks 807 (configured to hold overhangs 706). To attach the infusion set cap 1100 to the infusion set base 700, the cap 1100 can be placed thereover and rotated (e.g., clockwise) into position such that the post 704 fits within the shelf 806 and the overhangs 706 engage with the hooks 807. The latch 805 and tooth 707 can engage to hold the cap 1100 and base 700 in rotational alignment with one another until a force is applied by the user (i.e., a counterclockwise force to the cap 1100), which can cause the tooth 707 to bend out of the way and allow for the release of the cap 1100 from the base 700 (e.g., after use).

Figure 16C:
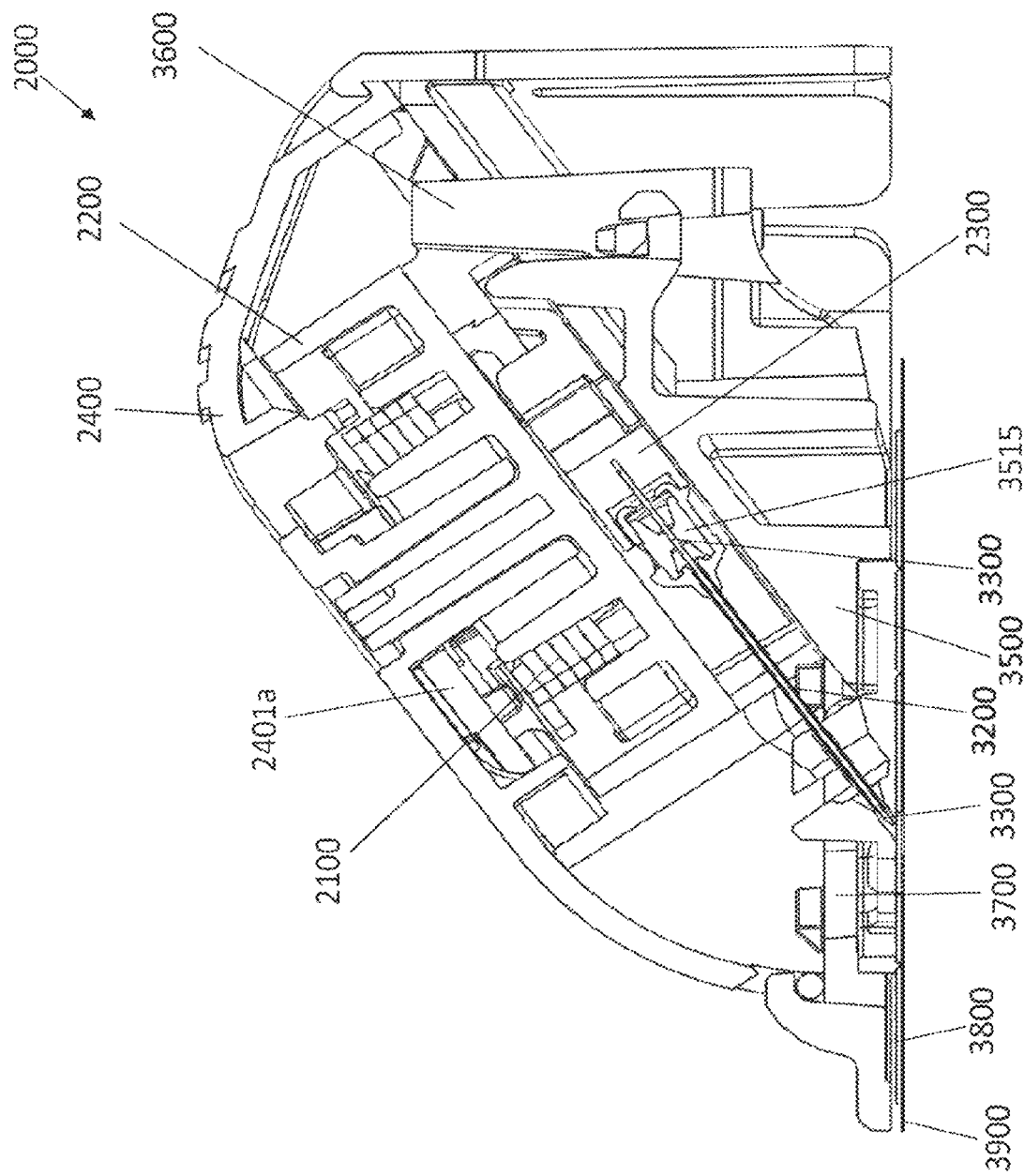
FIG. 16C is a cross-sectional view of the system of FIG. 16A prior to insertion of the cannula into the infusion set base.
Figure 20B:
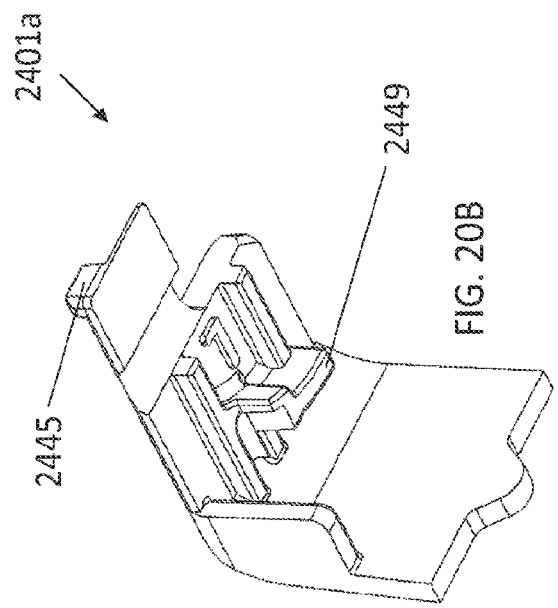
FIG. 20B is a bottom perspective view of the first button of FIG. 20A.
Figure 20D:
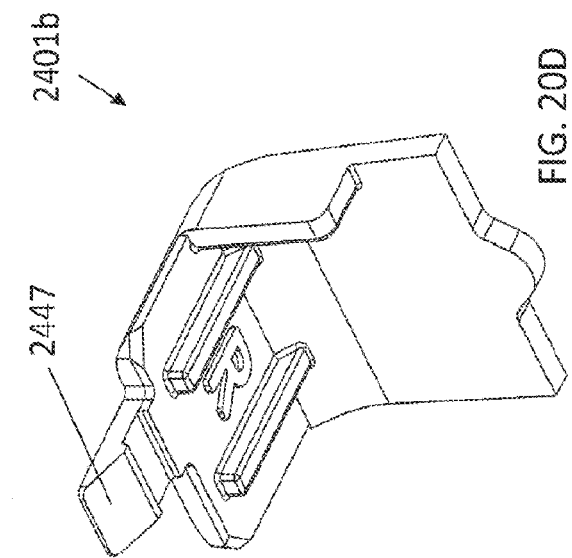
FIG. 20D is a bottom perspective view of the second button of FIG. 20C.
Figure 20A:
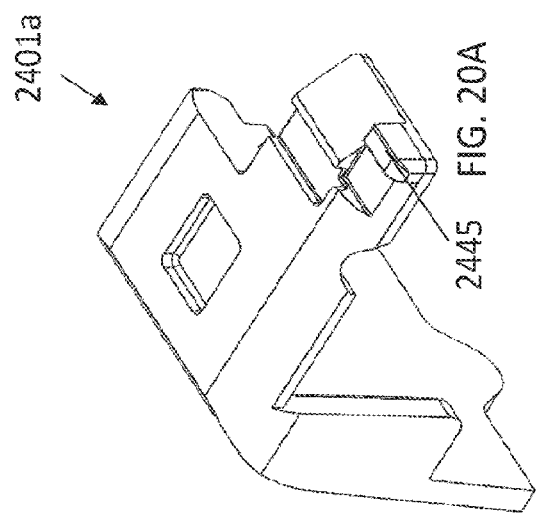
FIGS. 20A is a top perspective view of a first button of the system of FIGS. 16A-16C.
Figure 20C:
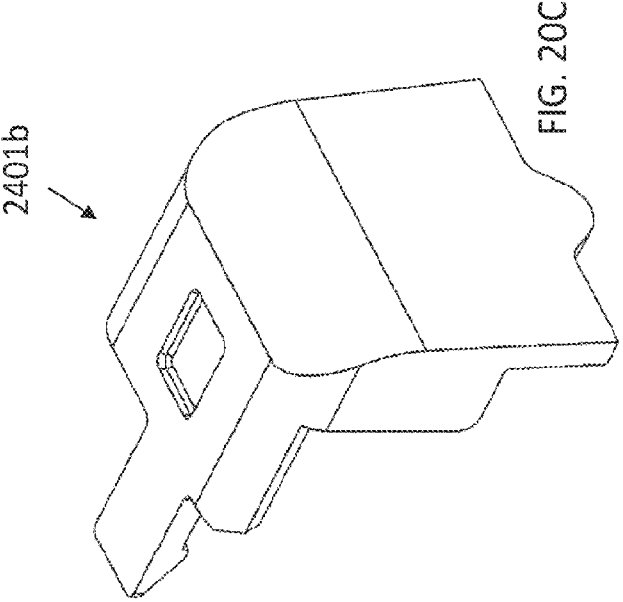
FIG. 20C is a top perspective view of a second button of the system of FIGS. 16A-16C.

Referring to FIGS. 16A-16C, another exemplary inserter and infusion set system 2000 similar to infusion set 1000 includes a top housing 2400 (with buttons 2401*a,b*), a torsion spring 2100, a drive wheel 2200, a linear slide 2300 with a stylet 3300, a bottom housing 2500, a lock ring 2600, an infusion set base 2700, an adhesive patch 2800 (with markers 2881, 2883) to adhere the infusion set base 2700 to the user, and an adhesive liner 2900 that can be removed to expose the adhesive patch 800. The inserter (top housing 2400, a torsion spring 2100, a drive wheel 2200, linear slide 2300, bottom housing 2500, and lock ring 2600) can be used to insert a cannula 3200 (with septum 3515) and adhere the infusion set base 2700 to the user, e.g., for infusion of insulin to the patient.

Referring to FIGS. 17A-17C, the drive wheel 2200 is similar to drive wheel 200 except that drive wheel 2200 includes an inner wall 2221 around which the spring 2100 is configured to wind. Radially extending overhangs 2223 on the inner wall 2221 ensure that the spring 2100 stays contained within the drive wheel 2200. Further, the external ramps 203 are replaced with a slot 2224 that is configured to interact with buttons 2401*a,b*. The post 204 is replaced with hook 2225, and the ends of the spring 2100 have hooks that curve radially outwards. Further, a ramped bump 2226 on the lower surface can help hold the slider to prevent it from moving until the inserter is activated. Drive wheel 2200 is otherwise similar to drive wheel 200 (for example, including pin 2205 for interaction with the linear slide).

Referring to FIGS. 18A-18B, the linear slide 2300 is similar to linear slide 300 except that the framework 2333 includes a curved portion 1111 curving radially outwards at the stylet port 2305. Additionally, the linear slide 2300 includes a solid bottom surface 2337 to provide enhanced strength of the slide 2300. The framework 2333 further includes posts 2301 (rather than slots 301) configured to engage with slotted rails in the bottom housing 2500. The framework 2333 also includes a tooth 2331 that is configured to interface with the barrel of the cannula to ensure that the barrel stays in the upright orientation (e.g., for alignment with the needle of the cap). The ramp 2302 for releasing the locking mechanism 2600 is further positioned on a side of the framework 2333 opposite to the stylet port 2305 (rather than on the same side). Additionally, the framework 2333 includes a curved wall 2332 extending into the elongate slot 2306 to help prevent (via interaction with the post 2205 of the drive wheel 2200) movement of the slider 2300 before activation. The framework 2333 also includes a cut-out 2334 on the top surface thereof to avoid interaction with the bump 2226 on the drive wheel 2200. The framework also includes an additional cut-out 2335 on the bottom surface thereof to travel over a detent on the bottom housing 2500 when retracting the stylet 3300. A cut-out 2336 in the solid bottom surface 2337 allows for a release clip on the bottom housing 2500 to pop up and lock the slider 2300 from moving at the end of travel (e.g., after the stylet 3300 has been fully retracted). A post 2338 extend radially outwards to help prevent the slider 2300 from rotating while traveling along the rails of the bottom housing 2500.

An exemplary sequence of the drive wheel 2200 (rotating counterclockwise) and linear slide 2300 (both shown simplified for clarity) moving axially along axis 1011 is shown in FIGS. 11A-G. At FIG. 11A, the drive wheel 2200 is charged and locked by the control (e.g., button), and the linear slide 2300 is in the ready position. At FIG. 11B, the drive wheel 2200 is unlocked and rotates counterclockwise, and the drive wheel 200 is allowed to accelerate with no load. At FIG. 11C, the drive wheel 2200 rotates such that the pin 2205 is in engagement with the linear slide 2330. At FIG. 11D, the drive wheel 2200 is rotated to the dwell transition, the linear slide 2300 is at the dwell transition, and the drive wheel 2200 rotates but the linear slide 2330 does not move axially (the dwell position is enabled by the curved bottom portion 1111 of the linear slide 2300). Accordingly, at FIG. 11E, the drive wheel 2200 is rotated partially through the dwell, and the linear slide 2300 remains at the same axial/dwell position (rotation of the pin 205 tracks the arc of the curved portion 1111 so as to keep the linear slide 2300 at the same axial position). Holding the linear slide 2300 (and thus the cannula) in the dwell position can advantageously provide additional time for the cannula to seat and lock within the infusion set base (e.g., via clips on the infusion set base that engage with the proximal barrel of the cannula). At FIG. 11F, the drive wheel 2200 is rotated completely through the dwell such that further movement of the pin 2205 will result in movement of the linear slide upwards for retraction of the stylet. At FIG. 11G, the drive wheel 2200 is rotated to the "stop" position (set by a stop on the housing), the linear side 2300 is in the completed position, and the stylet is retracted from the cannula into the housing.

Referring to FIGS. 19A-19B, the top housing 2400 is similar to top housing 400 except that the buttons 2401 (see FIGS. 20A-20D) are separate components (though they could be the same). Top housing 2400 additionally includes clips 2441 for engagement with and attachment to the bottom housing 2501. The top housing 2400 additionally includes arrows 2443 that can be used as an indicator for the user during application. As shown in FIGS. 20A-20D, the buttons 2401a can include hard stop features 2445 thereon that prevents the button from being pushed until the both buttons 2401a,b are pushed. Similarly, the button 2401b includes a ramp 2447 thereon to interface with the button 2401a. The underside of the button 2401a includes a wall 2449 that interfaces with the drive wheel 2200 to hold it in the locked position.

Referring to FIGS. 21A-21B, the bottom housing 2500 is similar to bottom housing 500 but includes hard stops 2551 to limit button travel (e.g., so as to avoid interference or contact with the linear slide 2300). The bottom housing 2500 further includes slots 2553 extending upwards from the bottom so as to provide shock dampening (e.g., if the housing 2500 is dropped). The bottom housing 2500 further includes a clip 2557 therein to keep the locking mechanism 2600 locked until released. Finally, the rails 2504 can be slots rather than extensions.

Referring to FIGS. 22A-22B, the locking mechanism 2600 can be similar to locking mechanism 1400 (of FIG. 14) except that it can include a bridge feature 2661 configured to interface with the clip 2557 on the bottom housing 2500.

Referring to FIGS. 23A-23B, the infusion set base 2700 can be similar to infusion set base 700 except that it can include tabs 2701 for engagement with the locking mechanism 2600. Additionally, the infusion set base 2700 can include a window 2771 therein for cannula viewing (e.g., so that the user can ensure that the cannula enters the skin).

Figure 25A:
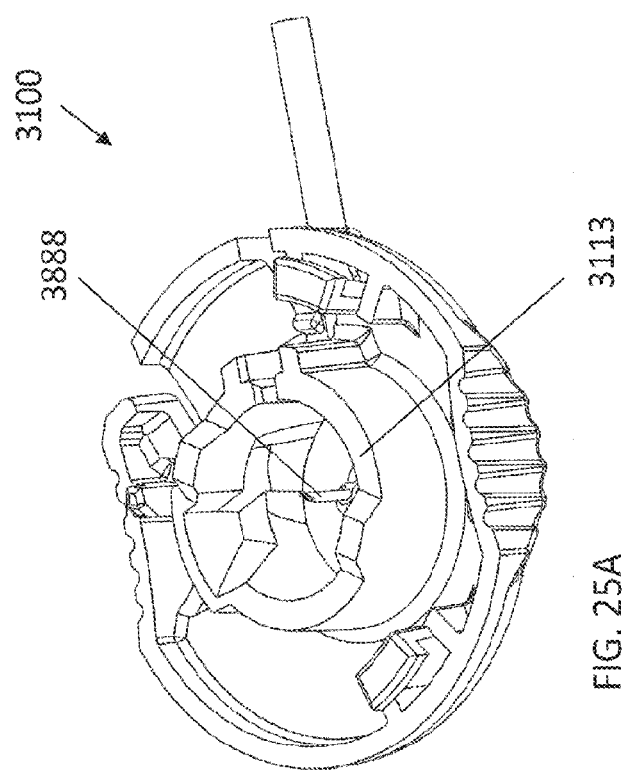
FIG. 25A is a bottom perspective view of an infusion set cap for use with the system of FIGS. 16A-16C.

Referring to FIGS. 24A-24B, the cannula 3200 can be similar to cannula 1200 except that the barrel 3212 can include a keying feature 3221 that can interact with the tooth 2331 on the slider 2300 to keep the barrel alignment and ensure that the side port 3216 is upright for insertion of the cap needle 3888 (see FIG. 25A). The barrel 3212 can further include an elongate tapered distal end 3223 to help prevent cannula migration within the infusion set base 2700 prior to activation.

Figure 25B:
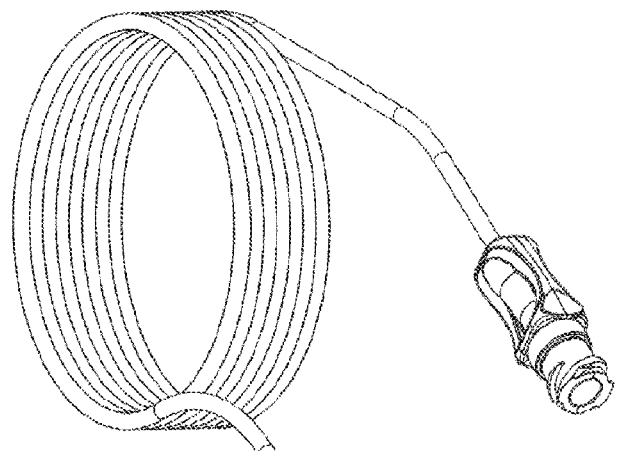
FIG. 25B is a top perspective view of an infusion set cap and tubing for use with the system of FIGS. 16A-16C.

Referring to FIGS. 25A-25B, the cap 3100 can be similar to cap 1100 except that the under surface thereof can include raised features 3113 configured to surround the needle 3888 to protect the user from the sharp tip when the cap 3100 is not attached to the base 2700. The cap 3100 additionally includes a marker 3115 configured to demonstrate alignment with the base 2700 during attachment and a window 3117.

An exemplary method of use of the system 2000 for infusion of fluids (e.g., insulin) into the body below the surface of the skin is shown in FIGS. 27A-27I. At FIG. 27A, the adhesive liner 2900 can be peeled away to expose the adhesive patch 2800 of the infusion set base 2700. At FIG. 27B, the inserter can be oriented so that the arrows 2443 on the high edge of the housing 2400/2500 point in the direction that the user wishes the tubing to run when actuated. At FIG. 27C, the inserter can be placed and adhered at the desired insertion site. At FIG. 27D, the buttons 2401a,b can be squeezed until the user hears or feels a click (as the inserter installs the cannula and releases the infusion set base 2700). At FIG. 27E, the inserter can be lifted away from the skin. At FIG. 27F, the adhesive patch 2800 can be smoothed around the infusion set base 2700. At FIGS. 27G-27H, the cap 3100 can be attached to the infusion set base 2700 that is adhered to the skin. To do so, the marker 3115 on the cap 3100 can be aligned with the marker first 2881 on the adhesive patch 2800. The cap 3100 can then be locked to the infusion set base 2700 by rotating the cap 3100 clockwise until the marker 3115 on the cap 3100 is aligned with the second marker 2883 on the adhesive patch 2800. Fluid can then be supplied to the tubing 2803 for delivery to the subcutaneous tissue of the user. Referring to FIG. 27I, the cap 3100 can be removed from the infusion set base 2700 by squeezing the latch 2805 inwards and rotating the cap 3100 clockwise.

Figure 4A:
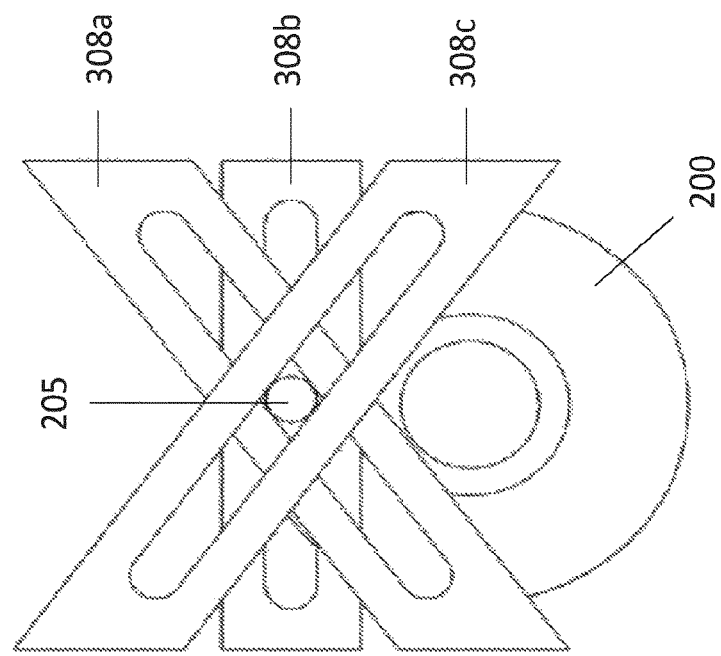
FIG. 4A is a bottom view of a drive wheel having a plurality of straight linear slides attached thereto.

In some embodiments, one or more linear slides can be used to control the release of the cannula (e.g., the rate and direction). For example, as shown in FIG. 4A, three straight linear slides 308a-308c can be positioned over pin 205 of the drive wheel 200. As another example and as shown in FIG. 4B, two curved linear slides 309a-309c can be positioned over pin 205 of the drive wheel. The linear slides can be stacked over one another and driven by a common engagement (i.e., pin 205) with the drive wheel 200. These embodiments with multiple linear slides can, for example provide multiple external engagements and/or multiple linear speeds.

In some embodiments, the inserters described herein can be used to simultaneously or consecutively insert multiple elongate bodies (e.g., cannulas) into the subcutaneous tissue. For example, referring to FIGS. 26A-D, where multiple linear slides are used, one elongate body 4200a,b (e.g., cannula and inner stylet) can be attached to and activated by each linear slide. Thus, FIG. 26A shows the first and second elongate bodies 4200a,b in a neutral starting position. As shown in FIG. 26B, as the drive wheel 5200 is rotated clockwise, the pin 5205 causes the first elongate body 4200a to move axially downwards (i.e., for insertion into the subcutaneous tissue). As shown in FIG. 26C, as the drive wheel 5200 is rotated further clockwise, the pin 5205 travels towards the nadir (lowest) point and causes the second elongate body 4200b to also move axially downwards (i.e., for insertion into the subcutaneous tissue). As shown in FIG. 26D, continued rotation of the drive wheel 5200 clockwise will result in the pin 5205 moving the first elongate body 4200a axially upwards (i.e., for retraction from the subcutaneous tissue). Retraction of the second elongate body 4200b occurs upon further rotation to the starting point (FIG. 26A). A single rotation (e.g., 360° or less) of the drive wheel can thus result in insertion and retraction of both elongate bodies 4200a,b. Additionally, in some embodiments, the direction of rotation can be reversed, i.e., in order to insert the second elongate body 4200b before the first elongate body 4200a.

In another embodiment, multiple elongate bodies can be attached to and activated by a single linear slide.

Where multiple elongate bodies are used, the elongate bodies can all be cannulas configured to deliver one or more medicaments (e.g., insulin and/or a hormone such as glucagon) and/or one or more of the elongate bodies can be configured to include a body analyte sensor (e.g., a continuous glucose monitoring sensor). In some embodiments where multiple elongate bodies are inserted, the multiple cannulas can be inserted at a distance of greater than 5 mm (e.g., greater than 7 mm, greater than 10 mm, or greater than 15 mm) from each other (e.g., so as to keep a cannula with a body analyte sensor far enough away from the cannula with the medicament to avoid contamination of the sensor with the medicament).

Figure 12B:
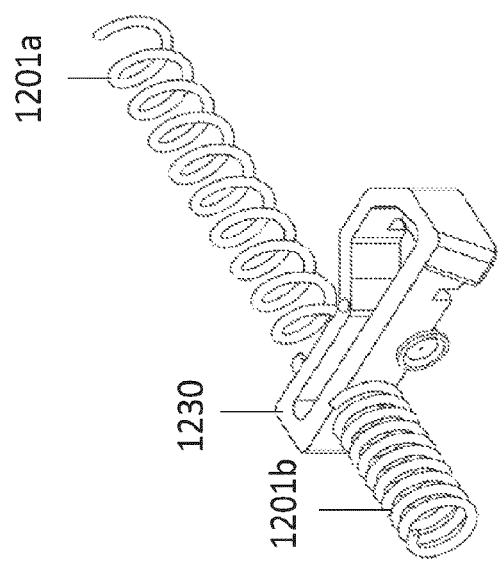

In some embodiments, the inserter described herein can include two or more linear or compression springs with one spring configured to act as a drive spring and another configured to act as a return spring. For example, as shown in FIGS. 12A-12B, the inserter can include a drive spring 1201a, a return spring 1210b, and a linear slide 1230 therebetween. In this embodiment, a drive wheel and rotational spring are not included. Rather, the linear slide 1230 moves due to the linear movement of the compression springs 1201a,b. That is, in FIG. 12A, the drive spring 1201a is charged (or compressed), the linear slide 1230 is locked, and the return spring 1201b is not charged (or is expanded). In this embodiment, as the spring rate of the drive spring 1201a decreases, the return spring 1201b is thereby charged. In FIG. 12B, the drive spring 1201a is released (or expanded), the linear slide 1230 has traveled to the nadir point for insertion of the cannula 1200 and stylet 1300, and the return spring 1201b is charged. The return spring 1201b, which is in engagement with the housing and the linear slide 1230, is positioned so as to retract the stylet 1300 from the cannula 1200 upon expansion, allowing a patent fluid path through the cannula. In some embodiments, the linear compression return spring can be unloaded and charged during insertion. In other embodiments, the linear compression return spring can be pre-loaded and then, at the end of the insertion motion, can be released (e.g., by mechanical release) to allow the retraction spring to activate to retract the stylet from the tissue.

Figure 13C:
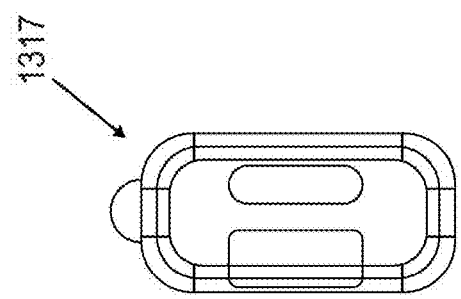
FIGS. 13A-13C show exemplary infusion sets that can be used with the springs and/or linear slides for an infusion system.
Figure 13B:
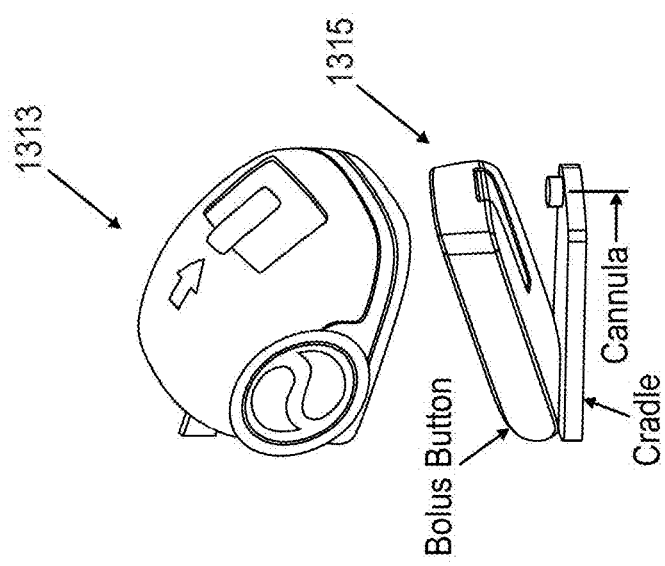
Figure 13A:
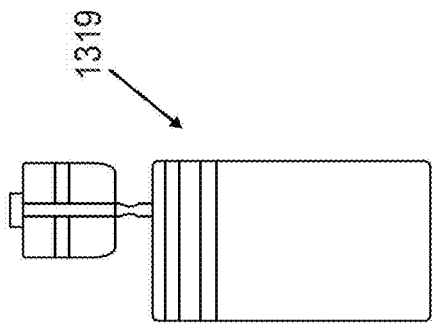

The spring and/or linear slide mechanisms described herein can be configured to be integrated into or made compatible with various types of infusion sets. Exemplary infusion sets are shown in FIGS. 13A-13C. As shown in FIG. 13A, a separate inserter can be used with a tubed infusion set 1319. As shown in FIG. 13B, a separate inserter 1313 can be used with an integrated patch 1315 (i.e., a wearable pump without an external tubing set). As shown in FIG. 13C, an integrated set 1317 can include both the infusion set and the inserter therein.

In some embodiments, the spring and/or linear slide mechanisms described herein can be embedded within another device having a different and separate function (e.g., inside of a wearable medicament pump).

In some embodiments, the infusion set base described herein can be configured as cradle that can be used, for example, for physical attachment of an entire pump, reservoir, and/or sensor (as opposed to attachment to only the infusion set cap). The infusion set base (configured as a cradle) can, as described herein, include mechanical features to lock the intermediate infusion set placement device into the inserter until completion of the cannula insertion cycle and can then be released therefrom for attachment of the pump, reservoir, or sensor. The infusion set base/cradle can include mechanical elements and features that: (1) removably attach the pump to the intermediate infusion set placement device; and (2) locate and provide a sterile attachment for fluid interconnect.

In some embodiments, an electromechanical release mechanism (e.g., inside the inserter or the infusion set) can be used to activate the cannula/stylet insertion and retraction (e.g., rather than a user-activated button). The electromechanical release mechanism can, for example, be a timing-based release and/or can be configured to be actuated remotely.

In any of the embodiments described herein, the inserter can be configured to fully retract the (hollow or solid) stylet from the cannula through the septum while the cannula remains in the tissue. Medicament can then be passed through the cannula for release to the subcutaneous tissue. Alternatively, in any of the embodiments described herein, the inserter can be configured to only partially retract the (hollow) stylet from the cannula through the septum while the cannula remains in the tissue. Medicament can then be passed through the stylet into the cannula for release to the subcutaneous tissue.

Any of the springs described herein can be replaced with other types of springs. For example, linear springs, coiled springs, extension springs, leaf springs, or torsion springs can be used.

In some embodiments, the inserter can be configured to adjust the depth of protrusion to allow medicament to be released in subcutaneous space at any chosen depth. In one embodiment, the angled surface of the bottom housing can have an adjustable angle. For example, a hinge at the front of the bottom housing can allow the angled of the slanted surface to change in relation to the bottom surface. By increasing the angle of insertion, the depth of cannula insertion can be increased. Conversely, by decreasing the angle of insertion, the depth of cannula insertion can be decreased. In another embodiment, linear slide can have a variable limit for travel to adjust cannula depth. In another embodiment, the center shaft of the top housing that holds the drive wheel can be on rails so that its location in location to the rest of the top housing can be adjusted to as to adjust the depth of cannula insertion.

In some embodiments, the inserters described herein can be constant speed and have a single linear slide. For example, the inserter can contain a source of stored energy (e.g., torsion spring under tension), a rotational element (e.g., drive wheel), a retention mechanism to lock the rotational element in a charged state (e.g., one or more release buttons), a motion transfer element to convert rotational energy to linear energy with a constant amplitude and constant frequency (e.g., a linear slide as described with respect to FIGS. 10A-10E), a cannula and inserter needle assembly attached to the linear slide in a manner to allow retention of the inserter stylet by the linear slide and release of the cannula during the insertion cycle (e.g., the cannula can be retained by the infusion set base and the stylet can be retracted into the insert), a mechanical component to first retain the infusion set base and then release the infusion set upon completion of the insertion cycle (e.g., the locking ring), and housing elements to contain and align the above mentioned functions (e.g., the top housing and bottom housing). The infusion set base can include mechanical features to lock the base into the inserter until completion of the insertion cycle and then release the base to remain affixed to the skin on removal of the inserter. The affixment can be a suitable skin adhesive containing a biocompatible adhesive side to affix to the skin and a breathable membrane allowing air and moisture transfer during wear. This adhesive can be permanently affixed to the infusion set base to secure the base to the skin in a manner such that normal wear and skin movement does not adversely affect the function of the infusion set.

In some embodiments, the inserters described herein can be variable speed and have a single linear slide. For example, the inserter can include a source of stored energy (e.g., a torsion spring under tension), a rotational element (e.g., a drive wheel), a motion transfer element to convert rotational energy to linear energy with a constant amplitude and varying frequency (e.g., a linear slide with a curved section as described with respect to FIGS. 11A-11G), a cannula and inserter needle assembly attached to the linear slide in a manner to allow retention of the inserter needle (stylet) by the linear slide and release of the cannula during the insertion cycle (e.g., the cannula can be retained by the infusion set base, and the stylet can be retracted into the inserter), a mechanical component to first retain the infusion set base and then release the infusion set upon completion of the insertion cycle (e.g., a locking ring), and housing elements to contain and align the above mentioned functions (e.g., the top housing and bottom housing). The infusion set base can contain mechanical features to lock the base into the inserter until completion of the insertion cycle and then release the base to remain affixed to the skin on removal of the inserter. The affixment can be a suitable skin adhesive containing a biocompatible adhesive side to affix to the skin and a breathable membrane allowing air and moisture transfer during wear. This adhesive can be permanently affixed to the infusion set base to secure the base to the skin in a manner such that normal wear and skin movement does not adversely affect the function of the infusion set.

In some embodiments, the inserters described herein can be constant speed and have multiple linear slides. For example, the inserter can include a source of stored energy (e.g., a torsion spring under tension), a rotational element (e.g., a drive wheel), a multiplicity of motion transfer elements to convert rotational energy to linear energy with a constant amplitude and constant frequency (e.g., the linear slide configuration shown in FIG. 4A), a cannula and inserter needle assembly attached to the linear slide in a manner to allow retention of the inserter needle (stylet) by the linear slide and release of the cannula during the insertion cycle (e.g., the cannula can be retained by the infusion set base, and the stylet can be retracted into the inserter), a mechanical component to first retain the infusion set base and then release the infusion set upon completion of the insertion cycle (e.g., a locking Ring), and housing elements to contain and align the above mentioned functions (e.g., the top housing and bottom housing). The infusion set base can contain mechanical features to lock the base into the inserter until completion of the insertion cycle and then release the base to remain affixed to the skin on removal of the inserter. The affixment can be a suitable skin adhesive containing a biocompatible adhesive side to affix to the skin and a breathable membrane allowing air and moisture transfer during wear. This adhesive can be permanently affixed to the infusion set base to secure the base to the skin in a manner such that normal wear and skin movement does not adversely affect the function of the infusion set.

In some embodiments, the inserters described herein can have variable speed and multiple linear slides. For example, the inserter can include a source of stored energy (e.g., a torsion spring under tension), a rotational element (e.g., a drive wheel); a multiplicity of motion transfer elements to convert rotational energy to linear energy with a constant amplitude and varying frequency (e.g., the linear slides shown in FIG. 4B a cannula and inserter needle assembly attached to the linear slide in a manner to allow retention of the inserter needle (stylet) by the linear slide and release of the cannula during the insertion cycle (e.g., the cannula can be retained by the infusion set base, and the stylet can be retracted into the inserter), a mechanical component to first retain the infusion set base and then release the infusion set upon completion of the insertion cycle (e.g., a locking Ring), and housing elements to contain and align the above mentioned functions (e.g., the top housing and bottom housing). The infusion set base can contain mechanical features to lock the base into the inserter until completion of the insertion cycle and then release the base to remain affixed to the skin on removal of the inserter. The affixment can be a suitable skin adhesive containing a biocompatible adhesive side to affix to the skin and a breathable membrane allowing air and moisture transfer during wear. This adhesive can be permanently affixed to the infusion set base to secure the base to the skin in a manner such that normal wear and skin movement does not adversely affect the function of the infusion set.

Although primarily described here as being used for insertion of one or more cannulas, it should be understood that the inserters and systems described herein can be used to subcutaneously insert a variety of insertable bodies, such as needles, sensors, or other elongate bodies.

It should be understood that features described herein with respect to one embodiment can be combined or substituted for features described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for delivering fluid to a user transcutaneously, the system comprising:
  a drive wheel;
  a torsion spring disposed within the drive wheel;
  a linear slide engaged within the drive wheel and having a stylet attached thereto;
  a cannula; and
  an infusion set base configured to removably couple to an inserter housing and to attach to a user's skin;
  wherein the torsion spring is energized such that, when actuated, the torsion spring delivers a spring force on the drive wheel to rotate the drive wheel, and wherein rotation of the drive wheel causes the linear slide engaged with the drive wheel to move axially to drive the stylet and cannula into a user's skin, and wherein the infusion set base is configured to engage with the cannula as the cannula is driven into the user's skin so as to hold the cannula in the user's skin as the stylet is retracted and the system includes an automatic release mechanism configured to automatically decouple the inserter housing from the infusion set base following insertion of the cannula.

2. The system of claim 1, wherein the drive wheel is configured to rotate a first amount to axially drive the infusion cannula into the user's skin with a stylet, and wherein the drive wheel is configured to rotate a second additional amount to retract the stylet from the user's skin.

3. The system of claim 2, wherein the first amount is approximately 180 degrees, and wherein the second additional amount is approximately 180 degrees.

4. The system of claim 2, wherein the torsion spring is configured to supply all energy required to both drive the infusion cannula and retract the stylet.

5. The system of claim 2, wherein the torsion spring, drive wheel, linear slide, and cannula are all configured to be housed within an inserter housing prior to insertion of the stylet and cannula into the user's skin, and wherein the stylet and cannula extend out of the housing for insertion into the user's skin.

6. The system of claim 1, wherein the infusion set base includes an adhesive on at least one surface thereof configured to attach the infusion set base to the user's skin.

7. The system of claim 1, wherein the automatic release mechanism comprises a post configured to engage with the linear slide as the linear slide moves axially, the infusion set base configured to decouple from the inserter as the linear slide moves the post.

8. The system of claim 1, wherein the automatic release mechanism comprises a plurality of arms configured to engage with the infusion set base to hold the infusion set base to the inserter prior to activation of the automatic release mechanism.

9. The system of claim 1, wherein the cannula is flexible.

10. The system of claim 1, further comprising a housing configured to house the torsion spring, drive wheel, linear slide, and cannula, wherein the housing comprises an angled surface therein upon which the drive wheel is rotational mounted so as to enable angled delivery of the stylet and cannula into the user's skin.

11. The system of claim 1, wherein the cannula further comprises a septum at the proximal end thereof, the septum configured to seal upon removal of the stylet from the cannula.

12. The system of claim 11, further comprising a fluid connection assembly configured to fluidically connect the cannula to a source of delivery fluid through the septum.

13. A system for delivering fluid to a user transcutaneously, the system comprising:
 a torsion spring;
 a drive wheel;
 a linear slide having a stylet attached thereto; and
 a cannula;
 wherein the torsion spring, when actuated, is configured to rotate the drive wheel to cause the linear slide to move axially to drive the stylet and cannula into a user's skin,
 the drive wheel comprises a pin and the linear slide comprises a framework having an elongate slot therein, the elongate slot configured to be positioned around the pin to transfer rotational movement of the drive wheel to axial movement of the linear slide.

14. The system of claim 13, wherein the framework comprises a curved portion extending radially outwards therefrom, the stylet attaching to the curved portion, further wherein rotation of the pin through the curved portion creates a dwell in movement of the linear slide.

15. A system for delivering fluid to a user transcutaneously, the system comprising:
 a cannula comprising a barrel and an elongate flexible member, wherein the barrel further includes a septum therein, the septum configured to allow passage of a stylet through the cannula and to self-seal as the stylet is removed from the cannula; and
 an infusion set base comprising a central port through which the elongate flexible member is configured to extend, the infusion set base configured to lock the barrel thereto.

16. The system of claim 15, further comprising an inserter configured to removably couple with the infusion set base, the inserter further configured to insert the cannula into the infusion set base.

17. The system of claim 16, wherein the inserter is further configured to retract the stylet from the cannula.

18. The system of claim 15, wherein the infusion set base further comprises one or more clips configured to open radially to allow the elongate flexible member to pass therethrough and to close radially around the barrel to lock the barrel thereto.

19. The system of claim 15, further comprising an inserter comprising a drive wheel and a linear slide, the drive wheel configured to rotate to cause the linear slide to move axially to drive the cannula into a user's skin.

20. The system of claim 19, wherein the drive wheel comprises a pin and the linear slide comprises a framework having an elongate slot therein, the elongate slot configured to be positioned around the pin to transfer rotational movement of the drive wheel to axial movement of the linear slide.

21. The system of claim 20, wherein the framework comprises a curved portion extending radially outwards therefrom, the stylet attaching to the curved portion, further wherein rotation of the pin through the curved portion creates a dwell in movement of the linear slide so as to allow time for the infusion set base to lock to the barrel.

22. The system of claim 15, further comprising an infusion set cap configured to interlock with the infusion set base, the infusion set cap comprising a needle configured to pierce the septum as the infusion set cap and infusion set base are mated.

23. The system of claim 22, wherein the needle is configured to pierce the septum at a different angle than the stylet.

24. The system of claim 23, wherein the needle is configured to pierce the septum at approximately a 10-65° degree angle relative to the stylet.

25. The system of claim 15, wherein the septum comprises an elastomer.

26. The system of claim 15, wherein the barrel compresses the septum radially and axially.

27. The system of claim 15, wherein the septum comprises a cylindrical outer wall and an H-shaped longitudinal cross-section.

* * * * *